United States Patent
Ebdrup et al.

(10) Patent No.: US 6,743,608 B2
(45) Date of Patent: Jun. 1, 2004

(54) PROCESS FOR THE PREPARATION OF SUBSTITUTED 3-PHENYL-PROPANOIC ACID ESTERS AND SUBSTITUTED 3-PHENYL-PROPANOIC ACIDS

(75) Inventors: Soren Ebdrup, Kobenhavn O (DK); Heinz-Josef W. Deussen, Soborg (DK); Magali Zundel, Soborg (DK)

(73) Assignee: Novo Nordisk Pharmaceuticals, Inc., Bagsvaerd (DK)

(*) Notice: Subject to any disclaimer, the term of this patent is extended or adjusted under 35 U.S.C. 154(b) by 0 days.

(21) Appl. No.: 10/131,876

(22) Filed: Apr. 24, 2002

(65) Prior Publication Data

US 2003/0054510 A1 Mar. 20, 2003

Related U.S. Application Data

(63) Continuation of application No. 09/633,890, filed on Aug. 7, 2000, now abandoned.
(60) Provisional application No. 60/148,504, filed on Aug. 12, 1999.

(30) Foreign Application Priority Data

Aug. 5, 1999 (DK) .................................. PA 1999 01100

(51) Int. Cl.[7] .......................... C12P 13/00; C12P 13/02; C12P 7/62; C12P 7/42; C12N 9/18
(52) U.S. Cl. ........................ 435/128; 435/129; 435/130; 435/135; 435/136; 435/146; 435/197; 435/198
(58) Field of Search ................................ 435/128, 129, 435/130, 135, 136, 146, 197, 198

(56) References Cited

U.S. PATENT DOCUMENTS 5,061,629 A    10/1991    Coffen et al. ................ 435/280
5,306,726 A  * 4/1994    Hulin .......................... 514/375

FOREIGN PATENT DOCUMENTS

EP          0 459 455 A2    12/1991
WO       WO9919313     * 1/1998

OTHER PUBLICATIONS

Haigh et al., Bioorganic & Medicinal Chemistry. vol. 7, pp. 821–830 (1991).
Abstract of Japanese Patent 1–281098 (A) Nov.
J. Bryan Jones, Tetrahedron, vol. 42. pp. 3351–3403 (1986).

* cited by examiner

*Primary Examiner*—Herbert J. Lilling
(74) *Attorney, Agent, or Firm*—Rosemarie R. Wilk-Orescan; Reza Green

(57) ABSTRACT

The present invention relates to a process comprising hydrolysis or trans esterification of one of the two enantiomeric forms of a racemic or enantiomerically enriched ester of formula I or IV by a higher rate than the other by an enzyme to give an ester and a acid (III) or two different esters (V) and (VI) with different R groups both with increased enantiomeric purity and a esterification process of a racemic or enantiomerically enriched acid (VII) by an enzyme to give an ester and an acid both with increased enantiomeric purity.

26 Claims, 1 Drawing Sheet

PROCESS FOR THE PREPARATION OF SUBSTITUTED 3-PHENYL-PROPANOIC ACID ESTERS AND SUBSTITUTED 3-PHENYL-PROPANOIC ACIDS

CROSS-REFERENCE TO RELATED APPLICATIONS

The application of U.S. application Ser. No. 09/633,890 filed Aug. 7, 2000 and now abandoned, and claims priority under 35 U.S.C. 119 of Danish application No. PA 1999 01100 filed on Aug. 5, 1999 and U.S. provisional application No. 60/148,504 filed on Aug. 12, 1999, the contents of which are fully incorporated herein by reference.

FIELD OF INVENTION

The present invention relates to a new process for the preparation of optically enriched substituted esters of 3-phenyl-propanoic acids and substituted 3-phenyl-propanoic acids.

BACKGROUND OF THE INVENTION

Yasuo Kato et. al. have shown that incubation of α-benzyloxycarboxylic esters with grown cells of the bacterium Corynebacterium equi afforded chiral esters via asymmetric hydrolysis (Tetrahedron Letters, Vol. 28, No.12, 1303–1306, 1987).

Japanese Patent Application No. 61-208680 describes methods for the production of optically active α-hydroxycarboxylic acid derivatives by the use of bacteria belonging to the genus Corynebacterium. In the patent application processes are described converting racemic esters (2 g/l) in culture solutions (where the microbe is capable of growing) during 24 to 65 h of shake culturing.

However, according to K. Faber in "Biotransformations in Organic Chemsitry", 4$^{th}$ Ed., Springer Veriag 1999, p. 10, the usage of a growing cell culture has a number of disadvantages vs. isolated enzymes, such as more difficult process control, the handling of large biomass in a chemical plant, and more by-product formation.

Japanese Patent Application No. 63-107536 describes the use of a few lipases for the production of optically active 2-hydroxycarboxylic acids and esters.

Jean-Marc Ricca et al. found that α-Chymotrypsin suspended in organic solvents was stereoselective with respect to the hydrolysis of L-amino acid derivatives, but no stereoselectivity was observed when α-hydroxy esters were used as substrates (J. Chem. Soc. Perkin Trans., Vol. 1, 1225–1233, 1993).

David Haigh et al. showed that a Rhizopus delemar lipase catalysed hydrolysis of methyl 3-[4-[2-[N-(benzoxazolyl)-N-methylamino]ethoxy]-phenyl]-2-methoxypropanoate affords the (R)-(+) and (S)-(−) isomers in >84% enantiomeric excess. (Bioorganic and Medicinal Chemistry vol. 7, 821–830, 1999).

However, to achieve such optical purity for the (S)-acid, double enzymatic resolution was necessary: The (S)-acid was isolated from the initial enzymatic hydrolysis, re-esterified, and enzymatically rehydrolysed.

As described by Collins Sheldrake Crosby (Chirality in Industry, 1992 section 1.3.1) it is a big advantage for large-scale production to process a minimum of material. To be able to do this the chiral purification needs to be performed as early as possible in a synthetic route. This is the opposite of what is seen in the Haigh reference but in line with the process described in this patent application. The overall process cost as e.g. environmental cost (less waste is generated), operating costs and material cost are in general lower for processes where the chiral separation is performed early in the synthesis as seen for the present invention.

It has recently been shown, that β-aryl-α-oxysubstituted alkylcarboxylic acids have hypolipidemic and antihyperglycemic uses (WO 99/19313).

The synthesis of these compounds involves several steps to achieve the pure enantiomeric form of the compounds, which show pharmacological activity.

WO 00/26200 discloses the synthesis of optical enriched β-aryl-α-oxysubstituted alkylcarboxylic acids and esters related to the compounds mentioned in WO 99/19313.

The object of the present invention is therefore to provide a new process involving an enzymatic resolution step for the preparation of optically enriched substituted esters of 3-phenyl-propanoic acids and substituted 3-phenyl-propanoic acids which process is adaptable to large scale manufacture, provides good yields and high purity and reduces the cost of manufacture as e.g. environmental cost (less waste is generated).

SUMMARY OF THE INVENTION

The present invention relates to a process comprising hydrolysis or trans-esterification of one of the two enantiomeric forms of a racemic or enantiomerically enriched ester of formula I or IV by a higher rate than the other by an enzyme to give an ester (II) and an acid (III) or two different esters (V) and (VI) with different R groups both with increased enantiomeric purity and an esterification process of a racemic or enantiomerically enriched acid (VII) by an enzyme to give an ester (IX) and an acid (VIII) both with increased enantiomeric purity.

The process can be used to synthesise important building blocks for the preparation of compounds active at the Peroxisome Proliferator-Activated Receptors (PPAR) like the ones described in WO 99/19313 and in Haigh et al. (Bioorganic and Medicinal Chemistry vol. 7. 821–830. 1999).

DETAILED DESCRIPTION OF THE INVENTION

Figure 1:
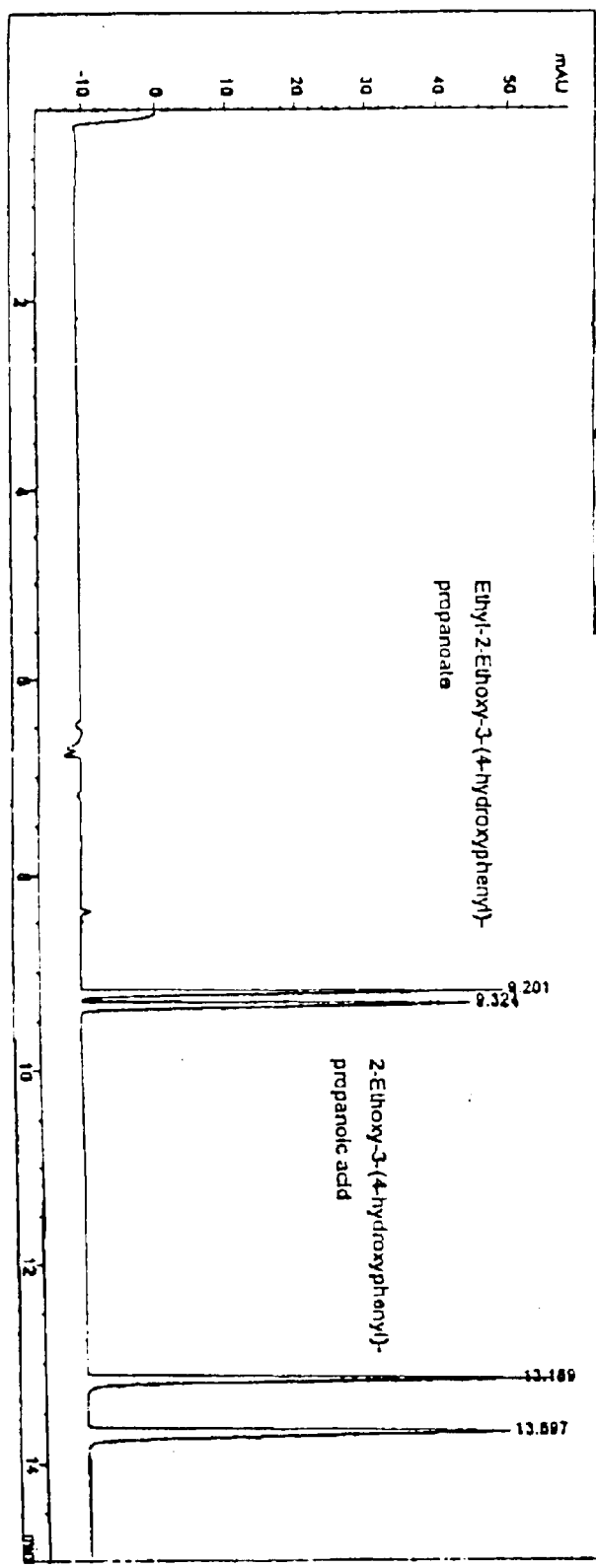
FIG. 1 shows an electropherogram of a mixture of ethyl (2R2RS)-2-ethoxy-3-(4-hydroxphenyl-propanoate and (2RS)-2-ethoxy-3-(4-hydroxyphenyl)propanoic acid (CCE method 2).

The process of the invention can be divided into three types of reaction schemes:

Process 1

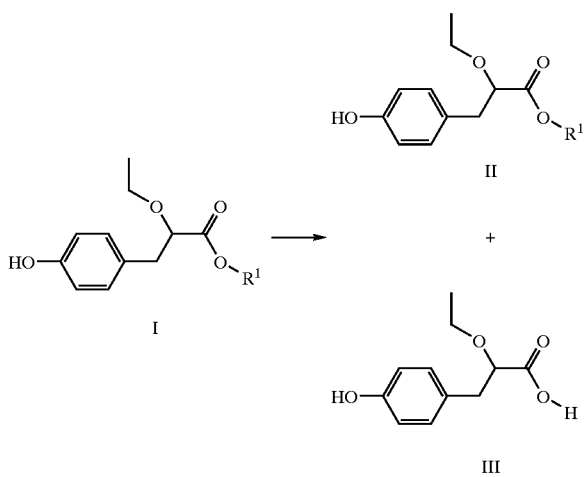

One of the two enantiomers of racemic or enantiomerically enriched (I) is hydrolysed at a higher rate than the other in a solvent with an enzyme to give a product mixture of an acid (III) and an ester (II) both with increased enantiomeric purity wherein $R^1$ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —CN, —OH, —SH, —COOH, $C_{1-6}$-alkoxy, $C_{1-6}$alkylthio, —$SCF_3$, —$OCF_3$, —$CONH_2$, —$CSNH_2$, —$NR^XR^Y$ wherein X and Y independently are defined as hydrogen or $C_{1-6}$-alkyl, or $R^1$ is optionally substituted with phenyl or phenoxy wherein phenyl or phenoxy is optionally substituted with one or more selected from halogen(s), —OH, —SH, —COOH, —$N^XR^Y$, —$CF_3$, —CN, $C_{1-4}$-alkyl, $C_{1-4}$-alkoxy, $C_{1-4}$-alkylthio, —$SCF_3$, —$OCF_3$, —$CONH_2$ or —$CSNH_2$.

Dependent on the enzyme applied the following product mixtures can be formed: optically enriched R (II) and S (III) or optically enriched S (II) and R (III).

Process 2

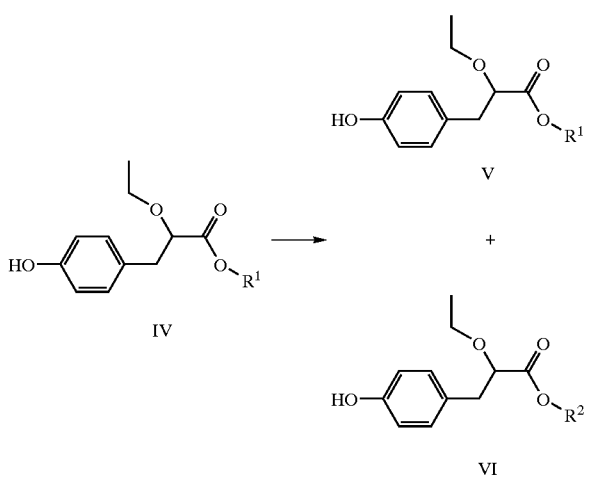

One of the two enantiomers of racemic or enantiomerically enriched (IV) is trans-esterified at a higher rate than the other in a solvent containing an appropriate alcohol $R^2$—OH or just in the appropriate alcohol without solvent with an enzyme to give a product mixture of two different esters (V) and (VI) both with increased enantiomeric purity wherein $R^1$ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —CN, —OH, —SH, —COOH, $C_{1-6}$-alkoxy, $C_{1-6}$-alkylthio, —$SCF_3$, —$OCF_3$, —$CONH_2$, —$CSNH_2$, —$NR^XR^Y$ wherein $R^X$ and $R^Y$ independently are defined as hydrogen or $C_{1-6}$-alkyl, or $R^1$ is optionally substituted with phenyl or phenoxy wherein phenyl or phenoxy is optionally substituted with one or more selected from halogen(s), —OH, —SH, —COOH, —$NR^XR^Y$, —$CF_3$, —CN, $C_{1-4}$-alkyl, $C_{1-4}$-alkoxy, $C_{1-4}$-alkylthio, —$SCF_3$, —$OCF_3$, —$CONH_2$ or —$CSNH_2$ and wherein $R^2$ is defined as $R^1$ provided that $R^2$ is different from the actual $R^1$ in the starting material.

Dependent on the enzyme applied the following product mixtures can be formed: enriched R (V) and S (VI) or enriched S (V) and R (VI).

Preferably, the two esters are so different that they easily can be separated by e.g. extraction e.g. a $R^1$ making the starting material (IV) soluble in water and an $R^2$ making the product (VI) soluble in a not water miscible organic solvent.

Process 3

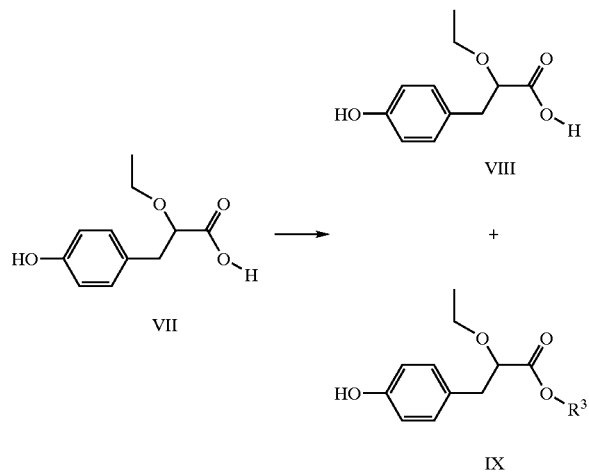

One of the two enantiomers of racemic or enantiomerically enriched (VII) is esterified at a higher rate than the other in a solvent containing an appropriate alcohol $R^3$—OH or just in the appropriate alcohol without solvent with an enzyme to give a product mixture of an acid (VIII) and an ester (IX) both with increased enantiomeric purity wherein $R^3$ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —CN, —OH, —SH, —COOH, $C_{1-6}$-alkoxy, $C_{1-6}$-alkylthio, —$SCF_3$, —$OCF_3$, —$CONH_2$, —$CSNH_2$, —$NR^XR^Y$ wherein X and Y independently are defined as hydrogen or $C_{1-6}$-alkyl, or $R^3$ is optionally substituted with phenyl or phenoxy wherein phenyl or phenoxy is optionally substituted with one or more selected from halogen(s), —OH, —SH, —COOH, —$NR^XR^Y$, —$CF_3$, —CN, $C_{1-4}$-alkyl, $C_{1-4}$-alkoxy, $C_{1-4}$-alkylthio, —$SCF_3$, —$OCF_3$, —$CONH_2$ or —$CSNH_2$.

Dependent on the enzyme applied the following product mixtures can be formed: enriched R (VIII) and S (IX) or enriched S (VIII) and R (IX).

Preferably, the two esters can easily be separated by e.g. extraction.

Process 1, Process 2, and Process 3 may be combined in order to enhance the enantiomeric purity. Enantiomerically enriched III may be used as starting material VII in Process 3; enantiomerically enriched II or IX may be used as starting material IV in Process 2; enantiomerically enriched V, VI, and IX may be used as starting material I in Process 1.

The terms "$C_{1-n'}$-alkyl" wherein n' can be from 2 through 30, as used herein, alone or in combination is intended to include those alkyl groups of the designated length in either a linear or branched or cyclic configuration, represents e.g. cyclopropyl, cyclobutyl, cyclopentyl, cyclohexyl, cycloheptyl and cyclooctyl and the like. Typical $C_{1-30}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like.

The terms "$C_{2-n'}$-alkenyl" wherein n' can be from 3 through 30, as used herein, represents an olefinically unsaturated branched or straight group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl and the like.

The terms "$C_{2-n'}$-alkynyl" wherein n' can be from 3 through 30, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 30, as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{1-6}$-alkoxy" as used herein, alone or in combination is intended to include those $C_{1-6}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentoxy, isohexoxy and the like. Examples of cyclic alkoxy are cyclopropyloxy, cyclobutyloxy, cyclopentyloxy, cyclohexyloxy and the like.

The term "$C_{1-6}$-alkylthio" as used herein, alone or in combination, refers to a straight or branched or cyclic monovalent substituent comprising a $C_{1-6}$-alkyl group linked through a divalent sulfur atom having its free valence bond from the sulfur atom and having 1 to 6 carbon atoms e.g. methylthio, ethylthio, propylthio, butylthio, pentylthio and the like. Examples of cyclic alkylthio are cyclopropylthio, cyclobutylthio, cyclopentylthio, cyclohexylthio and the like.

As used herein, the phrase "5 or 6 membered heterocyclic group" means a group containing from one to four N, O or S atom(s) or a combination thereof, which heterocyclic group is optionally substituted at carbon or nitrogen atom(s) with halogen, —OH, —CF$_3$, —CN, $C_{1-4}$-alkyl, $C_{1-4}$-alkoxy, $C_{1-4}$-alkylthio, —SCF$_3$, —OCF$_3$, —CONH$_2$, —CSNH$_2$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-membered heterocycles with four heteroatoms.

In the present context, the term "protease" is intended to mean any hydrolase, peptidase, proteinase or enzyme having proteolytic activity as comprised in EC 3.4-3.11 and any modification thereof, which modification have retained the activity of the enzyme. The enzyme having protease activity may be derived by means involving the use of a microorganism or by recombinant means.

Suitable proteases according to the present invention include those of animal, vegetable or microbial origin. Microbial origin is preferred. Chemically modified or protein engineered mutants are included. The protease may be a serine protease or a metallo protease, e.g. an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Other examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120,123, 167, 170, 194, 206, 218, 222, 224, 235 and 274.

Specific commercially available and useful protease enzymes include Subtilisin carlsberg sold under the trademark Alcalase®, Subtilisin 309 sold under the trademark Savinase®, Primase®, Duralase®, Esperase®, and Kannase® (Novo Nordisk A/S), Maxatase®, Maxacal®, Maxapem®, Properase®.

In the present context, the term "lipase" is intended to mean any hydrolase or enzyme having lipolytic activity as comprised in EC 3.1.1–3.1.7, and any modification thereof, which modification have retained the activity of the enzyme. The enzyme having lipase activity may be derived by means involving the use of a microorganism or by recombinant means.

The parent lipolytic enzyme according to the present invention may be prokaryotic, particularly a bacterial enzyme, e.g. from Pseudomonas. Examples are Pseudomonas lipases, e.g. from *P. cepacia* (U.S. Pat. No. 5,290,694, pdb file 1OIL), *P. glumae* (N Frenken et al. (1992), Appl. Envir. Microbiol. 58 3787–3791, pdb files 1TAH and 1QGE), *P. pseudoalcaligenes* (EP 334 462) and Pseudomonas sp. strain SD 705 (FERM BP4772) (WO 95/06720, EP 721 981, WO 96/27002, EP 812 910). The *P. glumae* lipase sequence is identical to the amino acid sequence of *Chro-*

*mobacterium viscosum* (DE 3908131 A1). Other examples are bacterial cutinases, e.g. from Pseudomonas such as *P. mendocina* (U.S. Pat. No. 5,389,536) or *P. putida* (WO 88/09367).

Alternatively, the parent lipolytic enzyme may be eukaryotic, e.g. a fungal lipolytic enzyme such as lipolytic enzymes of the Humicola family and the Zygomycetes family and fungal cutinases.

The Humicola family of lipolytic enzymes consists of the lipase from *H. lanuginosa* strain DSM 4109 and lipases having more than 50% homology with said lipase. The lipase from *H. lanuginosa* (synonym *Thermnomyces lanuginosus*) is described in EP 258 068 and EP 305 216, and has the amino acid sequence shown in positions 1–269 of SEQ ID NO: 2 of U.S. Pat. No. 5,869,438.

The Humicola family also includes the following lipolytic enzymes: lipase from *Penicillium camembertii* (P25234), lipase/phospholipase from *Fusarium oxysporum* (EP 130064, WO 98/26057), lipase from *F. heterosporum* (R87979), lysophospholipase from *Aspergillus foetidus* (W33009), phospholipase A1 from *A. oryzae* (JP-A 10-155493), lipase from *A. oryzae* (D85895), lipase/ferulic acid esterase from *A. niger* (Y09330), lipase/ferulic acid esterase from *A. tubingensis* (Y09331), lipase from *A. tubingensis* (WO 98/45453), lysophospholipase from *A. niger* (WO 98/31790), lipase from *F. solani* having an isoelectric point of 6.9 and an apparent molecular weight of 30 kDa (WO 96/18729).

The Zygomycetes family comprises lipases having at least 50% homology with the lipase of *Rhizomucor miehei* (P19515). This family also includes the lipases from *Absidia reflexa, A. sporophora, A. corymbifera, A. blakesleeana, A. griseola* (all described in WO 96/13578 and WO 97/27276) and *Rhizopus oryzae* (P21811). Numbers in parentheses indicate publication or accession to the EMBL, GenBank, GeneSeqp or Swiss-Prot databases.

In the present context the term "esterase" is intended to mean any enzymes capable of hydrolyzing and forming an ester bond.

In the present context the term "cutinase" is intended to mean any enzymes capable of hydrolyzing the substrate cutin.

Examples of fungal cutinases according to the present invention are the cutinases of *Fusarium solani pisi* (S. Longhi et al., Journal of Molecular Biology, 268 (4), 779–799 (1997)) and *Humicola insolens* (U.S. Pat. No. 5,827,719).

The term "solvent" as used herein refers to a solvent wherein the described reactions can take place.

In a preferred embodiment, the term "solvent" as used herein refers to an organic solvent, a mixture of organic solvents, an organic solvent or mixture of organic solvents and water containing salts or no salts buffered or non buffered, water containing salts buffered or not buffered a two phase system comprising an organic and an aqueous phase, emulsions and suspensions.

In another preferred embodiment, the term "solvent" as used herein refers to an organic solvent, a mixture of organic solvents, an organic solvent or mixture of organic solvents and water containing salts or no salts buffered or non buffered, water containing salts buffered or not buffered, a two phase system comprising of an organic and aqueous phase, emulsions and suspensions where "organic solvent" refers to e.g. hydrocarbons as e.g. hexane, cyclohexane, heptane, toluene, xylenes, ketones as e.g. tert-butyl-methylketone, methylisopropylketone, 2-butanone, acetone, 4-methyl-2-pentanone, ethers as e.g. diethylether, tert-butylmethylether, isopropyl-methylether, dioxane, dibutylether, dioxolane, anisole, and tetra-hydrofuran, nitrites as e.g. acetonitrile and 3-hydroxyproplonitrile, polar solvents as e.g. di-methylsulfoxide, N,N-dimethylformamide, N-methylpyrrolidone, sulfolane, dimethylpropylurea (DMPU), glyoxal, acids as e.g. acetic acid and formic acid, aldehydes as e.g. acetaidehyde, halogenated hydrocarbons as e.g. dichloromethane, trichloroethane, chloroform, chlorobenzene, dichlorobenzene, and dichloroethane, esters as e.g. ethyl acetate, isopropyl acetate, or tert-butyl acetate, straight or branched alcohols as e.g. 2-methyl-2-butanol, tert-butanol, methanol, ethanol, n-propanol, n-butanol, and iso-propanol.

In another preferred embodiment, the term "solvent" as used herein refers to buffered (e.g. phosphate, acetate), non buffered water, or buffered or non buffered water containing a water miscible organic solvent such as acetone, tetrahydrofuran, 2-propanol, ethanol, t-butanol, dimethylformamide, dimethylsulfoxide, or 2-methyl-2-pentanone or ethers, such as tert-butyl methyl ether, saturated or not saturated with water.

In another preferred embodiment of the invention, the term "solvent" as used herein refers to an organic solvent, a mixture of organic solvents, an organic solvent or mixture of organic solvents and water containing salts or no salts buffered or non buffered, water containing salts buffered or not buffered, a two phase system comprising of an organic and aqueous phase, emulsions and suspensions where "organic solvent" refers to e.g. hydrocarbons as e.g. hexane and heptane, ketones as e.g. tert-butyl-methylketone, 2-butanone and acetone, 2-methyl-2-pentanone, ethers as e.g. diethylether, tert-butylmethylether, isopropylmethylether and tetrahydrofuran, nitriles as e.g. acetonitrile and 3-hydroxypropionitrile, di-methylsulfoxide, N,N-dimethylformamide, N-methylpyrrolidone, sulfolane, dimethylpropylurea (DMPU), glyoxal, acids as e.g. acetic acid and formic acid, aldehydes as e.g. acetaldehyde, halogenated hydrocarbons as e.g. dichloromethane and dichloroethane, esters as e.g. tert-butyl acetate, straight or branched alcohols as e.g. 2-methyl-2-butanol, tert-butanol, methanol, ethanol, propanol or iso-propanol.

In another preferred embodiment of the invention, the term "solvent" as used herein refers to buffered (such as phosphate, acetate), non buffered water, or buffered or non buffered water containing an organic solvent such as acetonitrile or 2-methyl-2-pentanone.

In a preferred embodiment of the invention, the enzymatic hydrolysis according to Process 1 runs between pH 3–9 at 5–80° C. in buffered or non-buffered water optionally added an organic water miscible co-solvent.

In a preferred embodiment of the invention, the enzymatic hydrolysis according to Process 1 runs between pH 3–9 at 10–50° C. in buffered or non-buffered water optionally added an organic water miscible co-solvent.

In a preferred embodiment of the invention, the enzymatic hydrolysis according to Process 1 runs between pH 3–9 at 10–50° C. in buffered or non-buffered water optionally added an organic water miscible co-solvent as e.g. acetone, tetrahydrofuran, 2-propanol, ethanol, t-butanol, dimethylformamide.

In a preferred embodiment of the invention, the enzymatic hydrolysis according to Process 1 runs between pH 3–9 at 10–50° C. in buffered or non-buffered water optionally added an organic water miscible co-solvent selected from acetone, tetrahydrofuran, 2-propanol, ethanol, t-butanol, dimethylformamide.

In another preferred embodiment of the invention, the enzymatic hydrolysis according to Process 1 runs between pH 4–8 at 10–50° C. in buffered or non-buffered water optionally added an organic water miscible co-solvent.

In another preferred embodiment of the invention, the enzymatic hydrolysis according to Process 1 runs between pH 4–8 at 10–50° C. in buffered or non-buffered water optionally added an organic water miscible co-solvent as e.g. acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 4–8 at 10–50° C. in buffered or non-buffered water optionally added an organic water miscible co-solvent selected from acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 5–8 at 20–40° C. in buffered or non-buffered water optionally added an organic water miscible co-solvent.

In another preferred embodiment of the invention, the enzymatic hydrolysis according to Process 1 runs between pH 5–8 at 20–40° C. in buffered or non-buffered water optionally added an organic water miscible co-solvent as e.g. acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 5–8 at 20–40° C. in buffered or non-buffered water optionally added an organic water miscible co-solvent selected from acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 5–8 at 20–30° C. in buffered or non-buffered water optionally added an organic water miscible co-solvent.

In another preferred embodiment of the invention, the enzymatic hydrolysis according to Process 1 runs between pH 5–8 at 20–30° C. in buffered or non-buffered water optionally add-added an organic water miscible co-solvent as e.g. acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 5–8 at 20–30° C. in buffered or non-buffered water optionally added an organic water miscible co-solvent selected from acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 5–7 at 20–30° C. in buffered or non-buffered water optionally added an organic water miscible co-solvent.

In another preferred embodiment of the invention, the enzymatic hydrolysis according to Process 1 runs between pH 5–7 at 20–30° C. in buffered or non-buffered water optionally added an organic water miscible co-solvent as e.g. acetone, tetrahydrofuran, 2-propanol, ethanol, t-butanol, dimethylformamide, dimethylsulfoxide.

In another preferred embodiment of the invention, the enzymatic hydrolysis according to Process 1 runs between pH 5–7 at 20–30° C. in buffered or non-buffered water optionally added an organic water miscible co-solvent selected from acetone, tetrahydrofuran, 2-propanol, ethanol, t-butanol, dimethylformamide, dimethylsulfoxide.

In another preferred embodiment of the invention, the enzymatic esterification according to Process 3 runs at 15–90° C. in ethers or hydrocarbons or ketones or halogenated hydrocarbons.

In another preferred embodiment of the invention, the enzymatic esterification according to Process 3 runs at 15–90° C. in ethers or hydrocarbons.

In another preferred embodiment of the invention, the enzymatic esterification according to Process 3 runs at 15–90° C. in alcohols.

In another preferred embodiment of the invention, the enzymatic esterification according to Process 3 runs at 15–90° C. in the alcohol, which is used as the nucleophile in the esterification reaction.

In another preferred embodiment of the invention, the enzymatic esterification according to Process 3 runs at 15–90° C. in methanol, or 2-propanol, or ethanol, or 1-propanol.

In another preferred embodiment of the invention, the enzymatic esterification according to Process 3 runs at 30–85° C. in ethers or hydrocarbons.

In another preferred embodiment of the invention, the enzymatic esterification according to Process 3 runs at 30–85° C. in ethers as tert-butyl methyl ether.

In another preferred embodiment of the invention, the enzymatic esterification according to Process 3 runs at 50–60° C. in tert-butyl methyl ether.

In another preferred embodiment $R^1$ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —OH, —SH, —COOH, $C_{1-6}$-alkoxy, $C_{1-6}$-alkylthio, —$CONH_2$, —$NR^XR^Y$ wherein X and Y independently are defined as hydrogen or $C_{1-6}$-alkyl, or $R^1$ is optionally substituted with phenyl or phenoxy wherein phenyl or phenoxy is optionally substituted with one or more selected from halogen(s), —OH, —SH, —COOH, —$NR^XR^Y$, —$CF_3$, $C_{1-4}$-alkyl, $C_{1-4}$-alkoxy, $C_{1-4}$-alkylthio, —$CONH_2$.

In another preferred embodiment $R^2$ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —OH, —SH, —COOH, $C_{1-6}$-alkoxy, $C_{1-6}$-alkylthio, —$CONH_2$, —$NR^XR^Y$ wherein X and Y independently are defined as hydrogen or $C_{1-6}$-alkyl, or $R^2$ is optionally substituted with phenyl or phenoxy wherein phenyl or phenoxy is optionally substituted with one or more selected from halogen(s), —OH, —SH, —COOH, —$NR^XR^Y$, —$CF_3$, $C_{1-4}$-alkyl, $C_{1-4}$-alkoxy, $C_{1-4}$-alkylthio, —$CONH_2$.

In another preferred embodiment $R^3$ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —OH, —SH, —COOH, $C_{1-6}$-alkoxy, $C_{1-6}$-alkylthio, —$CONH_2$, —$NR^XR^Y$ wherein X and Y independently are defined as hydrogen or $C_{1-6}$-alkyl, or $R^3$ is optionally substituted with phenyl or phenoxy wherein phenyl or phenoxy is optionally substituted with one or more selected from halogen(s), —OH, —SH, —COOH, —$NR^XR^Y$, —$CF_3$, $C_{1-4}$-alkyl, $C_{1-4}$-alkoxy, $C_{1-4}$-alkylthio, —$CONH_2$.

In another preferred embodiment $R^1$ is straight or branched $C_{1-30}$-alkyl, straight or branched $C_{2-30}$-alkenyl, straight or branched $C_{2-30}$-alkynyl, straight or branched $C_{4-30}$-alkenynyl each of which is optionally substituted with one or more selected from halogen(s), —OH, —SH, $C_{1-6}$-alkoxy, $C_{1-4}$-alkylthio, or $R^1$ is optionally substituted with phenyl or phenoxy.

In another preferred embodiment $R^2$ is straight or branched $C_{1-30}$-alkyl, straight or branched $C_{2-30}$-alkenyl, straight or branched $C_{2-30}$-alkynyl, straight or branched $C_{4-30}$-alkenynyl each of which is optionally substituted with one or more selected from halogen(s), —OH, —SH, $C_{1-6}$-alkoxy, $C_{1-6}$-alkylthio, or $R^2$ is optionally substituted with phenyl or phenoxy.

In another preferred embodiment $R^3$ is straight or branched $C_{1-30}$-alkyl, straight or branched $C_{2-30}$-alkenyl, straight or branched $C_{2-30}$-alkynyl, straight or branched $C_{4-30}$-alkenynyl each of which is optionally substituted with one or more selected from halogen(s), —OH, —SH, $C_{1-6}$-alkoxy, $C_{1-6}$-alkylthio, or $R^3$ is optionally substituted with phenyl or phenoxy.

In another preferred embodiment $R^1$ is straight or branched $C_{1-30}$-alkyl, straight or branched $C_{2-30}$-alkenyl, straight or branched $C_{2-30}$-alkynyl, straight or branched $C_{4-30}$-alkenynyl each of which is optionally substituted with one or more selected from —OH, —SH, $C_{1-6}$-alkoxy, $C_{1-6}$-alkylthio.

In another preferred embodiment $R^2$ is straight or branched $C_{1-30}$-alkyl, straight or branched $C_{2-30}$-alkenyl, straight or branched $C_{2-30}$-alkynyl, straight or branched $C_{4-30}$-alkenynyl each of which is optionally substituted with one or more selected from —OH, —SH, $C_{1-6}$alkoxy, $C_{1-6}$-alkylthio.

In another preferred embodiment $R^3$ is straight or branched $C_{1-30}$-alkyl, straight or branched $C_{2-30}$-alkenyl, straight or branched $C_{2-30}$-alkynyl, straight or branched $C_{4-30}$-alkenynyl each of which is optionally substituted with one or more selected from —OH, —SH, $C_{1-6}$alkoxy, $C_{1-6}$-alkylthio.

In another preferred embodiment $R^1$ is straight or branched $C_{1-12}$-alkyl, straight or branched $C_{2-12}$-alkenyl, straight or branched $C_{2-12}$-alkynyl, straight or branched $C_{4-10}$-alkenynyl each of which is optionally substituted with one or more selected from $CF_3$, —OH, —SH, $C_{1-6}$-alkoxy, $C_{1-6}$-alkylthio.

In another preferred embodiment $R^2$ is straight or branched $C_{4-20}$-alkyl, straight or branched $C_{6-30}$-alkenyl, straight or branched $C_{6-30}$-alkynyl, straight or branched $C_{8-30}$-alkenynyl each of which is optionally substituted with one or more selected from $CF_3$, —OH, —SH, $C_{1-6}$-alkoxy, $C_{1-6}$-alkylthio.

In another preferred embodiment $R^3$ is straight or branched $C_{1-12}$-alkyl, straight or branched $C_{2-12}$-alkenyl, straight or branched $C_{2-12}$-alkynyl, straight or branched $C_{4-10}$-alkenynyl each of which is optionally substituted with one or more selected from $CF_3$, —OH, —SH, $C_{1-6}$-alkoxy, $C_{1-6}$-alkylthio.

In another even more preferred embodiment $R^1$ is straight or branched $C_{1-12}$-alkyl, straight or branched $C_{2-12}$-alkenyl, straight or branched $C_{2-12}$-alkynyl, straight or branched $C_{4-10}$-alkenynyl.

In another preferred embodiment $R^2$ is straight or branched $C_{4-20}$-alkyl, straight or branched $C_{6-30}$-alkenyl, straight or branched $C_{6-30}$-alkynyl, straight or branched $C_{8-30}$-alkenynyl.

In another preferred embodiment $R^3$ is straight or branched $C_{1-12}$-alkyl, straight or branched $C_{2-12}$-alkenyl, straight or branched $C_{2-12}$-alkynyl, straight or branched $C_{4-10}$-alkenynyl.

In another preferred embodiment $R^1$ is straight or branched $C_{1-12}$-alkyl optionally substituted with one or more selected from $C_{1-6}$-alkoxy, $C_{1-6}$-alkylthio.

In another preferred embodiment $R^2$ is straight or branched $C_{4-20}$-alkyl optionally substituted with one or more selected from $C_{1-6}$-alkoxy, $C_{1-6}$-alkylthio.

In another preferred embodiment $R^3$ is straight or branched $C_{1-12}$-alkyl optionally substituted with one or more selected from $C_{1-6}$-alkoxy, $C_{1-6}$-alkylthio.

In another preferred embodiment $R^1$ is straight or branched $C_{1-12}$-alkyl optionally substituted with one or more selected from $C_{1-6}$alkoxy.

In another preferred embodiment $R^2$ is straight or branched $C_{4-20}$-alkyl optionally substituted with one or more selected from $C_{1-6}$-alkoxy.

In another preferred embodiment $R^3$ is straight or branched $C_{1-12}$-alkyl optionally substituted with one or more selected from $C_{1-6}$-alkoxy.

In another preferred embodiment $R^1$ is straight or branched $C_{1-10}$-alkyl optionally substituted with one or more selected from $C_{1-6}$alkoxy.

In another preferred embodiment $R^2$ is straight or branched $C_{8-20}$-alkyl optionally substituted with one or more selected from $C_{1-6}$-alkoxy.

In another preferred embodiment $R^3$ is straight or branched $C_{1-10}$-alkyl optionally substituted with one or more selected from $C_{1-6}$alkoxy.

In another preferred embodiment $R^1$ is methyl, ethyl, 1-propyl, 2-propyl, 1-hexyl, or ethoxyethyl.

In another preferred embodiment $R^2$ is n-butyl, n-hexyl, n-decyl or 3-methyl-1-butyl.

In another preferred embodiment $R^3$ is straight or branched $C_{1-12}$-alkyl, straight or branched $C_{2-12}$-alkenyl, each of which is optionally substituted with one or more selected from halogen(s), —CN, $C_{1-6}$-alkoxy, $C_{1-6}$-alkylthio.

In another preferred embodiment $R^3$ is methyl, ethyl, 1-propyl, 2-propyl, 1-butyl, 1-pentyl, 1-hexyl, 1-heptyl, 1-octyl, 1-decanyl, 1-docecyl, 3-methyl-1-butyl, 4-methyl-1-pentyl, ethoxyethyl, 4,4,4-trifluorobutyl, 2-(methylmercapto)ethyl, 5-hexen-1-yl, 3-cyanopropyl, 3,3-dimethyl-1-butyl, 3-chloro-1-propyl, citronellyl, 3-cyclohexyl-1-propyl, 3-phenylpropyl, 3-(4-hydroxyphenyl)propyl.

In another preferred embodiment $R^3$ is methyl, ethyl, 1-propyl, 2-propyl, 1-butyl, 1-pentyl, 1-hexyl, 1-heptyl, 1-octyl, 1-decanyl, 1-docecyl, 3-methyl-1-butyl, 4-methyl-1-pentyl, ethoxyethyl, 3,3-dimethyl-1-butyl, 3-cyclohexyl-1-propyl, 3-phenylpropyl.

In another preferred embodiment $R^2$ is methyl, ethyl, 1-propyl, 2-propyl, 1-butyl, or ethoxyethyl and $R^1$ and $R^3$ independently are straight or branched $C_{6-30}$-alkyl.

In another preferred embodiment $R^1$ and $R^3$ independently are methyl, ethyl, n-propyl, 2-propyl, butyl, or ethoxyethyl and $R^2$ is straight or branched $C_{6-30}$-alkyl.

In another preferred embodiment $R^1$ is methyl, ethyl, 1-propyl, 2-propyl, 1-hexyl, or ethoxyethyl and $R^2$ is n-butyl, n-hexyl, n-decyl or 3-methyl-1-butyl.

In another preferred embodiment $R^2$ is methyl, ethyl, 1-propyl, 2-propyl, 1-hexyl, or ethoxyethyl and $R^1$ is n-butyl, n-hexyl, n-decyl or 3-methyl-1-butyl.

In another preferred embodiment $R^1$ is straight or branched $C_{1-6}$-alkyl, straight or branched $C_{2-8}$-alkenyl, straight or branched $C_{2-8}$-alkynyl, straight or branched $C_{4-10}$-alkenynyl each of which is optionally substituted with one or more selected from $CF_3$, —OH, —SH, $C_{1-6}$-alkoxy, $C_{1-6}$-alkylthio.

In another preferred embodiment $R^3$ is straight or branched $C_{1-6}$-alkyl, straight or branched $C_{2-8}$-alkenyl, straight or branched $C_{2-8}$-alkynyl, straight or branched $C_{4-10}$-alkenynyl each of which is optionally substituted with one or more selected from $CF_3$, —OH, —SH, $C_{1-6}$-alkoxy, $C_{1-6}$-alkylthio.

In another preferred embodiment $R^1$ is straight or branched $C_{1-6}$-alkyl, straight or branched $C_{2-6}$-alkenyl, straight or branched $C_{2-8}$-alkynyl, straight or branched $C_{4-10}$-alkenynyl.

In another preferred embodiment $R^3$ is straight or branched $C_{1-6}$-alkyl, straight or branched $C_{2-8}$-alkenyl, straight or branched $C_{2-8}$-alkynyl, straight or branched $C_{4-10}$-alkenynyl.

In another preferred embodiment $R^1$ is straight or branched $C_{1-10}$-alkyl optionally substituted with one or more selected from $C_{1-6}$-alkoxy, $C_{1-6}$-alkylthio.

In another preferred embodiment $R^3$ is straight or branched $C_{1-6}$-alkyl optionally substituted with one or more selected from $C_{1-6}$-alkoxy, $C_{1-6}$-alkylthio.

In another preferred embodiment $R^3$ is methyl, ethyl, 1-propyl, 2-propyl, 1-butyl, 1-pentyl, 1-hexyl, 1-heptyl, 1-octyl, 1-decanyl, or 1-dodececyl.

In another preferred embodiment of the present invention the enzyme is a protease.

In another preferred embodiment of the invention the protease is a commercial protease sold under the trademark Alcalase® (produced by submerged fermentation of a strain of *Bacillus licheniformis*), Subtilisin 147 sold under the trademark Esperase® (produced by submerged fermentation of an alkalophilic species of Bacillus), pepsin from Rhizo mucor meihei sold under the trademark Rennilase® (produced by submerged fermentation of a non-pathogenic strain of *Mucor miehei*), subtilisin 309 sold under the trademark Savinase® (produced by submerged fermentation of a genetically modified strain of Bacillus), e.g. the variants disclosed in the international Patent Application published as WO 92/19729, and a protein-engineered variant of Savinase®, Subtilisin 309 M121A, S189E sold under the trademark Durazym®. Also Subtilisin 309 M216S sold under the trademark, Everlase® and Kannase® are useful. All the mentioned commercial proteases are produced and sold by Novo Nordisk A/S, DK-2880 Bagsvaerd, Denmark. Further useful commercial proteases are MAXATASE® from International Bio-Synthetics, Inc. (The Netherlands) and proteases made by Genencor International, Inc., according to one or more of the following patents: Caldwell et al, U.S. Pat. Nos. 5,185,258, 5,204,015 and 5,244,791, e.g. Subrilisin PB92 S99G, V102N sold under the trademark Properase®. The patent references disclosed in the above paragraph are hereby incorporated in their entireties in this patent application.

Other preferred serine-proteases are proteases from Nocardiopsis, Aspergillus, Rhizopus, *Bacillus alcalophilus*, *B. cereus, N. natto, B. vulgatus, B. mycoide*, and subtilisins from Bacillus, especially proteases from the species Nocardiopsis sp. and *Nocardiopsis dassonvillei* such as those disclosed in the International Patent Application published as WO 88/03947, especially proteases from the species Nocardiopsis sp., NRRL 18262, and *Nocardiopsis dassonvillei*, NRRL 18133. Yet other preferred proteases are the serine proteases from mutants of *Bacillus subtilisins* disclosed in the International Patent Application No. PCT/DK89/00002 and in the International Patent Application published as WO 91/00345, and the proteases disclosed in EP 415 296.

Another preferred class of proteases are the metalloproteases of microbial origin. Conveniently, conventional fermented commercial proteases are useful. Examples of such a commercial protease is Neutrase® (Zn) (produced by submerged fermentation of a strain of *Bacillus subtilis*), which is produced and sold by Novo Nordisk A/S, DK-2880 Bagsvaerd, Denmark. The patent references disclosed in the above paragraph are hereby incorporated in their entireties in this patent application.

Other preferred commercial protease enzyme preparations are Bactosol® WO and Bactosol® SI, available from Sandoz AG, Basle, Switzerland; Toyozyme®, available from Toyo Boseki Co. Ltd., Japan; and Proteinase K® (produced by submerged fermentation of a strain of Bacillus sp. KSM-K16), available from Kao Corporation Ltd., Japan.

Still other preferred proteases include Protease A (see European Patent Application 130,756, published Jan. 9, 1985); Protease B (see European Patent Application Serial No. 87303761.8, filed Apr. 28, 1987, and European Patent Application 130,756, Bott et al, published Jan. 9, 1985). The patent references disclosed in the above paragraph are hereby incorporated in their entireties in this patent application.

In another preferred embodiment of the present invention the protease is selected from the following:
Protease 2 (or Aspergillopepsin I) from *Aspergillus aculeatus*, a variant of Savinase from *Bacillus clausii* sold under the trademark Kannases®,
Trypsin like protease from *Fusarium Oxysporum*,
Alp protease (or oryzin) from *Aspergillus Oryzae*,
Protease 2A from *Aspergillus Oryzac*,
C-component from *Bacillus Licheniformis*,
Protease 1 (or Aspergillopepsin II) from *Aspergillus Aculeatus*,
NpI protease (or Neutral proteinase I or Fungalysin) from *Aspergillus Oryzae*,
NpII protease from *Aspergillus Oryzae*,
Pepsin A protease from *Aspergillus Oryzae*,
PD 498 protease from Bacillus sp.,
Glycine specific protease from Papaya,
alpha-chymotrypsine type II from bovine pancreas,
aipha-chymotrypsine type VII from bovine pancreas,
Proteinase 2A from *Aspergillus Oryzae*,
Protease from *Pseudomonas putida*, sold under the trademark, Novozym 180®,
Proteinase 6 from *Aspergillus Oryzae*,
Flavourzyme® from *Aspergillus Oryzae*.

In another preferred embodiment of the present invention the protease is produced by or can be isolated from Aspergillus, Bacillus, Fusarium, Papaya, bovine pancreas.

In another preferred embodiment of the present invention the protease is produced by or can be isolated from *Aspergillus aculeatus, Bacillus clausii, Fusarium Oxysporum, Aspergillus Niger, Aspergillus Oryzae, Bacillus Licheniformis*, Bacillus sp., Papaya, bovine pancreas.

In another preferred embodiment of the present invention the enzyme is a lipase.

In another preferred embodiment of the present invention the enzyme is a lipase selected from yeast, e.g. Candida, lipases, bacterial, e.g. Pseudomonas or Bacillus, lipases; or fungal, e.g. Humicola or Rhizopus, lipases. More specifically, suitable lipases may be the *Rhizomucor miehei lipase* (e.g. prepared as described in EP 238 023; available from Novo Nordisk under the trade name Lipozyme™), Thermomyces lanuginosa lipase e.g. prepared as described in EP 305 216 (available from Novo Nordisk under the trade name Lipolase™), *Humicola insolens* lipase *Humicola lanuginosa* lipase, *Pseudomonas stutzeri* (eg. ATCC 19.154) lipase, *Pseudomonas cepacia* lipase, *Candida antarctica* lipase A or B, or lipases from rGPL, *Absidia blakesleena, Absidia corymbifera, Fusarium solani, Fusarium oxysporum, Penicillum cyclopium, Penicillum crustosum, Penicillum expansum, Rhodotorula glutinis, Thiarosporella phaseolina, Rhizopus microsporus, Sporobolomyces shibatanus, Aureobasidium pullulans, Hansenula anomala, Geotricum penicillatum, Lactobacillus curvatus, Brochothrix thermosohata, Coprinus cinerius, Trichoderma harzanium, Trichoderma reesei, Rhizopus japonicus* or *Pseudomonas plantari*. Other examples of suitable lipases may be variants of any one of the lipases mentioned above, e.g. as described in WO 92/05249 or WO 93/11254. Also suitable lipase enzymes for usage herein include those described in Japanese Patent Application 53,20487, laid open to public inspection on Feb. 24, 1978. This lipase is available from Amano Pharmaceutical Co. Ltd., Nagoya, Japan, under the trade name Lipase P "Amano," herinafter referred to as "Amano-P." Other commercial lipases include Amano-CES, lipases ex Chromobacter viscosum, e.g. *Chromobacter viscosum* var. lipolyticum NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The patent references disclosed in the above paragraph are hereby incorporated in their entireties in this patent application.

In another preferred embodiment of the present the enzyme is a cutinase.

In a preferred embodiment of the present invention the cutinase is from the organisms *Fusarium solani pisi* (S. Longhi et al., Journal of Molecular Biology, 268 (4), 779–799 (1997)) or *Humicola insolens* (U.S. Pat. No. 5,827, 719).

In another preferred embodiment of the present invention the enzyme is a phospholipase.

In another preferred embodiment of the present invention the enzyme is an esterase.

In another preferred embodiment of the present invention the esterase is an esterase from rabbit liver, Sigma E-9636, an esterase from porcine liver, Sigma E-7259, an esterase from hog pancreas, an esterase from hog liver, an esterase type V-S from electric eel, or an esterase from *Pseudomonas putida*.

In another preferred embodiment of the present invention the esterase is ferulic acid esterase from *Aspergillus Oryzae*, or acetyl xylan esterase from *Aspergillus aculeatus* expressed in *Aspergillus Oryzae*.

In another preferred embodiment of the present invention the esterase is produced by Aspergillus.

In another preferred embodiment of the present invention the esterase is produced by *Aspergillus aculeatus*.

In another preferred embodiment of the present invention the esterase is produced by *Aspergillus oryzae*.

In another preferred embodiment of the present invention the esterase is produced by *Aspergillus niger*.

In another preferred embodiment of the present invention the esterase is produced by Pseudomonas.

In another preferred embodiment of the present invention the esterase is from a commercially available enzyme preparation expressed in *Aspergillus aculeatus*, or *Aspergillus oryzae*, or *Aspergillus niger* such as e.g. Pectinex™ Ultra SP-L, Pectinex™ BE, Flavourzyme™, Kojizyme™ 500 MG, Shearzyme™ 500L, Pectinex™ AFP L-2, Pectinex™ SMASH, Novozyme 188, Rheozyme® all available from Novo Nordisk A/S.

In another preferred embodiment of the present invention the esterase is obtained from fermentation of *Aspergillus oryzae* (IFO 4177 Institute for Fermentation, Osaka, Japan).

In another preferred embodiment of the present invention the esterase is obtained from fermentation of *Aspergillus aculeatus* (CBS database No. CBS590.94).

In another preferred embodiment of the present invention the enzyme is a hydrolytic enzyme mixture, which contains two or more hydrolytic enzymes, such as a protease, a lipase, an esterase, a cutinase, or a phospholipase or three or more proteases, lipases, esterases, cutinases, or phospholipases.

In another preferred embodiment in relation to Process 1, the enzyme is produced by or can be isolated from Rhizopus, Humicola, Bacillus, Bovine pancreas, Pseudomonas, Aspergillus, Trypsin or Fusarium.

In another preferred embodiment in relation to Process 1, the enzyme is an esterase.

In another preferred embodiment of the present invention in relation to Process 1 the esterase is produced by Aspergillus.

In another preferred embodiment of the present invention in relation to Process 1 the esterase is produced by *Aspergillus aculeatus*.

In another preferred embodiment of the present invention in relation to Process 1 the esterase is produced by *Aspergillus oryzae*.

In another preferred embodiment of the present invention in relation to Process 1 the esterase is produced by *Aspergillus niger*.

In another preferred embodiment of the present invention in relation to Process 1 the esterase is from a commercially available enzyme preparation expressed in *Aspergillus aculeatus*, or *Aspergillus oryzae*, or *Aspergillus niger* such as e.g. Pectinex™ Ultra SP-L, Pectinex™ BE, Flavourzyme™, Kojizyme™ 500 MG, Shearzyme™ 500L, Pectinex™ AFP L-2, Pectinex™ SMASH, Novozyme 188, Rheozyme® all available from Novo Nordisk A/S.

In another preferred embodiment of the present invention in relation to Process 1 the esterase is obtained from fermentation of *Aspergillus oryzae* (IFO 4177 Institute for Fermentation, Osaka, Japan).

In another preferred embodiment of the present invention in relation to Process 1 the esterase is obtained from fermentation of *Aspergillus aculeatus* (CBS database No. CBS590.94).

In another preferred embodiment in relation to Process 1, the enzyme is selected from:
Rhizomucor miehei lipase,
Humicola lanuginosa lipase,
Bacillus licheniformis protease sold under the trademark Esperase®,
(*Bacillus clausii* protease) Savinase®,
α-chymotrypsin from Bovine pancreas,
Protease from *Pseudomonar putida*, sold under the trademark Novozym 180®,
Proteinase 6 from Aspergillus sp.,
Flavourzyme® from *Aspergillus oryzae*.
Protease 1 (or Aspergillopepsin II) from *Aspergillus aculeatus* expressed in *Aspergillus oryzae* also containing secreted enzymes from *Aspergillus oryzae*,
Protease 2 (or Aspergillopepsin I) from *Aspergillus aculeatus* expressed in *Aspergillus oryzae* also containing secreted enzymes from *Aspergillus oryzae*, NpI protease (or Neutral proteinase I or Fungalysin) from *Aspergillus oryzae* expressed in *Aspergillus oryzae* also containing secreted enzymes from *Aspergillus oryzae*,
Trypsin like protease from *Fusarium oxysporum* expressed in *Aspergillus oryzae* also containing secreted enzymes from *Aspergillus oryzae*,
a pectin methyl esterase from *Aspergillus aculeatus* sold under the tradename Rheozyme®,
Alp. protease (or oryzin) from *Aspergillus oryzae* expressed in *Aspergillus oryzae* also containing secreted enzymes from *Aspergillus oryzae*,
Protease 2A from *Aspergillus oryzae*,
Pectinex Ultra SP-L® from *Aspergilus aculeatus*,
Pectinex BE 3L® from *Aspergillus niger*,
Kojizyme 500 MG® from *Aspergilus oryzae*,
Ferulic acid esterase from *Aspergillus oryzae*,
Acetyl xylan esterase from *Aspergillus aculeatus*,
Shearzyme® 500 L from *Aspergillus aculeatus*,
Pectinex AFP L-2®,
Pectinex SMASH®,
Novozym 188® from *Aspergillus niger*,
a variant of Savinase from *Bacillus clausii* sold under the tradename Kannase®,
Cutinase from *Humicola insolens*,
Hydrolytic enzyme mixture obtained from fermentation of *Aspergillus oryzae*.

In an even more preferred embodiment in relation to Process 1, the enzyme is selected from:
Protease 1 (or Aspergillopepsin II) from *Aspergillus aculeatus* expressed in *Aspergillus oryzae* also containing secreted enzymes from *Aspergillus oryzae*,
Protease 2 (or Aspergillopepsin I) from *Aspergillus aculeatus* expressed in *Aspergillus oryzae* also containing secreted enzymes from *Aspergillus oryzae*,
Protease NpI from *Aspergillus aculeatus*,
NpI protease (or Neutral proteinase I or Fungalysin) from *Aspergillus oryzae* expressed in *Aspergillus oryzae* also containing secreted enzymes from *Aspergillus oryzae*,
Trypsin like protease from *Fusarium oxysporum* expressed in *Aspergillus oryzae* also containing secreted enzymes from *Aspergillus oryzae*,
a pectin methyl esterase from *Aspergillus acaleatus* sold under the tradename, Rheozyme®,
Alp. protease (or oryzin) from *Aspergillus oryzae* expressed in *Aspergillus oryzae* also containing secreted enzymes from *Aspergillus oryzae*,
Protease 2A® from *Aspergillus oryzae*,
Pectinex Ultra SP-L® from *Aspergillus aculeatus*,
Pectinex BE 3L® from *Aspergillus niger*,
Kojizyme 500 MG® from *Aspergillus oryzae*,
Ferulic acid esterase from *Aspergillus oryzae*,
Acetyl xylan esterase from *Aspergillus aculeatus*,
Shearzyme 500 L® from *Aspergillus aculeatus*,
Pectinex AFP L-2®,
Pectinex SMASH®,
Novozym 188® from *Aspergillus niger*,
Kannase®, a variant of Savinase from *Bacillus clausii*,
Cutinase from *Humicola insolens*,
Hydrolytic enzyme mixture obtained from fermentation of *Aspergillus oryzae*.

In the most preferred embodiment in relation to Process 1, the enzyme is selected from:
Protease 1 (or Aspergillopepsin II) from *Aspergillus aculeatus* expressed in *Aspergillus oryzae* also containing secreted enzymes from *Aspergillus oryzae*,
Protease 2 (or Aspergillopepsin I) from *Aspergillus aculeatus* expressed in *Aspergillus oryzae* also containing secreted enzymes from *Aspergillus oryzae*,
Protease NpI from *Aspergillus aculeatus*,
NpI protease (or Neutral proteinase I or Fungalysin) from *Aspergillus oryzae* expressed in *Aspergillus oryzae* also containing secreted enzymes from *Aspergillus oryzae*,
Trypsin like protease from *Fusarium oxysporum* expressed in *Aspergillus oryzae* also containing secreted enzymes from *Aspergillus oryzae*,
a pectin methyl esterase from *Aspergillus aculeatus* sold under the tradename Rheozyme®,
Alp. protease (or oryzin) from *Aspergillus oryzae* expressed in *Aspergillus oryzae* also containing secreted enzymes from *Aspergillus oryzae*,
Protease 2A® from *Aspergillus oryzae*,
Pectinex Ultra SP-L® from *Aspergillus aculeatus*,
Pectinex BE 3L® from *Aspergillus niger*,
Kojizyme 500 MG® from *Aspergillus oryzae*,
Ferulic acid esterase from *Aspergillus oryzae*,
Acetyl xylan esterase from *Aspergillus aculeatus*,
Shearzyme 500L from *Aspergillus aculeatus*,
Pectinex AFP L-2®,
Pectinex SMASH®,
Novozym 188® from *Aspergillus niger*,
Hydrolytic enzyme mixture obtained from fermentation of *Aspergillus oryzae*.

In another preferred embodiment in relation to Process 2, the enzyme is from the Rhizopus family.

In another preferred embodiment in relation to Process 3, the enzyme is from the Rhizopus family.

In another preferred embodiment in relation to Process 2, the enzyme is *Rhizomucor miehei* lipase.

In another preferred embodiment in relation to Process 3, the enzyme is *Rhizomucor miehei* lipase.

In a preferred embodiment in relation to Process 1, $R^1$ is straight or branched $C_{1-6}$-alkyl or ethoxyethyl, the enzyme is a hydrolase or an esterase from *Aspergillus aculeatus* or *Aspergillus oryzae*, the pH of the reaction mixture is from 4 to 8, the reaction mixture contains water and from 0 to 15% organic solvent, and the temperature is from 15 to 40° C.

In an even more preferred embodiment in relation to Process 1, $R^1$ is straight or branched $C_{1-3}$-alkyl or ethoxyethyl, the enzyme is a hydrolase or an esterase from *Aspergillus aculeatus* or *Aspergillus oryzae*, the pH of the reaction mixture is from 5 to 7, the reaction mixture contains water and from 0 to 5% organic solvent, and the temperature is from 20 to 30° C.

EXAMPLES

The starting compounds can be prepared according to known literature procedures as Geoffrey G. Cox et al., Tetrahedron Letters, 35, 3139, 1994. A general description is given below:

2-Ethoxyethyl (2RS) 3-[4-(benzyloxy)phenyl]-2-ethoxypropanoate

The ester can be prepared by acid catalysed esterification of 3-[4-(benzyloxy)phenyl]-2-ethoxypropanoic acid with/in 2-ethoxyethanol. Isocratic HPLC method 2 (4.34 min.): 97.6%.

2-Propyl (2RS) 3-[4-(benzyloxy)phenyl]-2-ethoxypropanoate

The ester can be prepared by acid catalysed esterification of 3-[4-(benzyloxy)phenyl]-2-ethoxypropanoic acid with/in 2-propanol. Isocratic HPLC method 2 (4.96 min.): 98.4%.

Hexyl (2RS) 3-[4-(benzyloxy)phenyl]-2-ethoxypropanoate

The ester can be prepared by acid catalysed esterification of 3-[4-(benzyloxy)phenyl]-2-ethoxypropanoic acid with/in 1-hexanol. Isocratic HPLC method 2 (8.57 min.): 92.2%.

Ethyl (2RS) 2-ethoxy-3-(4-hydroxyphenyl)propanoate

The title compound can be prepared as described by Geoffrey G. Cox et al. for the methyl ester. Isocratic HPLC method 2 (2.88): 95.6%; $^1$H-NMR (CDCl$_3$) δ: 1.18 (dt, 6H); 2.93 (d, 2H); 3.38 (m, 1H); 3.60 (m, 1H); 4.01 (t, 1H); 4.15 ((q, 2H); 6.01 (bs, 1H); 6.72 (d, 2H); 7.06 (d, 2H).

2-Ethoxyethyl (2RS) 2-ethoxy-3-(4-hydroxyphenyl)propanoate

The de-benzylated ester was prepared by a standard palladium on charcoal catalytic low pressure hydrogenation in ethanol of 2-ethoxyethyl (2RS) 3-[4-(benzyloxy)phenyl]-2-ethoxypropanoate. Isocratic HPLC method 2 (2.85 min.): 99.6%; $^1$H-NMR (CDCl$_3$) δ: 1.17 (dt, 6H); 2.95 (dd, 2H); 3.32 (m, 1H); 3.51 (q, 2H); 3.55–3.68 (m, 3H); 4.01 (t,1H); 4.25 (t, 2H); 5.92 (s, 1H); 6.72 (d, 2H); 7.08 (d, 2H).

2-Propyl (2RS) 2-ethoxy-3-(4-hydroxyphenyl)propanoate

The de-benzylated ester was prepared by a standard palladium on charcoal catalytic low pressure hydrogenation in ethanol of 2-Propyl (2RS) 3-[4-(benzyloxy)phenyl]2-ethoxypropanoate. Isocratic HPLC method 2 (3.0 min.): 99.0%; $^1$H-NMR (CDCl$_3$) δ: 1.19 (dt, 6H); 2.93 (d, 2H); 3.38 (m, 1H); 3.59 (m, 1H); 3.96 (t, 1H); 5.03 (m, 1H); 5.63 (bs, 1H); 6.72 (d, 2H); 7.10 (d, 2H).

Hexyl (2RS) 2-ethoxy-3-(4-hydroxyphenyl)propanoate

The de-benzylated ester was prepared by a standard palladium on charcoal catalytic low pressure hydrogenation in ethanol of hexyl (2RS) 3-[4-(benzyloxy)phenyl]-2-ethoxypropanoate. Isocratic HPLC method 2 (3.9 min.): 98.0%; $^1$H-NMR (CDCl$_3$) δ:=0.89 (t, 3H), 1.19 (t, 3H); 1.28 (m, 6H), 1.59 (m, 2H), 2.93 (d, 2H); 3.38 (m, 1H); 3.59 (m, 1H); 3.98 (t, 1H); 4.07 (t, 2H), 5.65 (bs, 1H), 6.73 (d, 2H), 7.09 (d, 2H).

(2RS) 3-(4-hydroxyphenyl)-2-ethoxy-propanoic acids

The title compounds were prepared from the corresponding esters by basic hydrolysis using standard procedures.

Chromatographic methods:

Isocratic HPLC method 1

Conditions:

| | |
|---|---|
| Column: | 250 × 4.0 mm, 5 mm C-18 YMC-Silica 120 Å |
| Flow: | 0.9 ml/min |
| Detector wavelength: | 220 nm. |
| Run time: | 30 min. |
| HPLC eluent: | |

50% acetonitrile at pH 3:

Isocratic HPLC method 2

Conditions:

| | |
|---|---|
| Column: | 250 × 4.0 mm, 5 mm C-18 YMC-Silica 120 Å |
| Flow: | 0.9 ml/min |
| Detector wavelength: | 220 nm. |
| Run time: | 30 min. |
| HPLC eluent: | |

90% methanol at pH 7 (pH adjusted with triethylamine and phosphoric acid)

Gradient HPLC method 1 (ethyl, 2-propyl, ethoxyethyl esters and the corresponding acids)

Conditions:

| | |
|---|---|
| Column: | Nucleosil C18 60*4 |
| Detector wavelength: | 225 nm/275 nm |

HPLC eluent:

| | |
|---|---|
| A: | Water with trifluoroacetic acid 0.01% |
| B: | Acetonitrile with trifluoroacetic acid 0.01% |

Timetable:

| time (min) | B % | Flow (ml/mn) |
|---|---|---|
| 0 | 0 | 1.8 |
| 0.01 | 0 | 2.7 |
| 6 | 100 | 2.7 |
| 6.2 | 100 | 2.7 |
| 6.3 | 0 | 2.7 |
| 6.9 | 0 | 2.7 |
| 7 | 0 | 1.8 |

Gradient HPLC method 2 (ethyl and decyl esters)

Conditions:

| | |
|---|---|
| Column: | Nucleosil C18 60*4 |
| Detector wavelength: | 225 nm/275 nm |
| Run time: | 55 min. |

HPLC eluent:

| | |
|---|---|
| A: | Water with trifluoroacetic acid 0.01% |
| B: | Acetonitrile with trifluoroacetic acid 0.01% |

Timetable:

| time (min) | B % | Flow (ml/mn) |
|---|---|---|
| 0 | 0 | 1.8 |
| 0.01 | 0 | 2.7 |
| 2.7 | 45 | 2.7 |
| 4 | 100 | 2.7 |
| 5.4 | 100 | 2.7 |
| 55 | 0 | 1.8 |

Gradient HPLC method 3 (ethyl ester and the corresponding acid)

Conditions:

| | |
|---|---|
| Column: | 250 × 4.0 mm, 5 mm C-18 YMC-Silica 120 Å |
| Detector wavelength: | 250 nm |
| Run time: | 40 min. |

HPLC eluent:

| | |
|---|---|
| A: | 80% Water with phosphoric acid 0.1%/20% acetonitrile |
| B: | Acetonitrile with phosphoric acid 0.1% |

Timetable:

| time (min) | B % | Flow (ml/mn) |
|---|---|---|
| 0 | 0 | 1.0 |
| 25 | 75 | 1.0 |
| 30 | 75 | 1.0 |
| 31 | 0 | 1.0 |
| 40 | 0 | 1.0 |

Sample Preparation for Chiral HPLC Methods

A sample of the reaction mixture (200 μl) was extracted with ethyl acetate (200 μl). The organic phase was evaporated and dissolved in a mixture of n-heptane and 2-propanol (85/15) (200 μl).

Chiral HPLC method 1 (ethyl ester)

Conditions:

| | |
|---|---|
| Column: | Chiracel OD 250*4.6 |
| Flow: | 1 ml/min |
| Detector wavelength: | 225/275 nm. |
| Run time: | 35 min. |
| HPLC eluent: | n-Heptane/2-propanol/acetic acid (95:5:0.1) |

Chiral HPLC method 2 (ethoxyethyl ester)

Conditions:

| | |
|---|---|
| Column: | Chiracel OD 250*4.6 |
| Flow: | 1 ml/min |
| Detector wavelength: | 225/275 nm. |
| Run time: | 45 min. |
| HPLC eluent: | |
| A: | n-Heptane/2-propanol/acetic acid (90:10:0.1) |
| B: | n-Heptane/acetic acid 0.1% |
| A:B (60:40) | |

Chiral HPLC method 3 (2-propyl ester)

Conditions:

| | |
|---|---|
| Column: | Chiralpak AS 250*4.6 |
| Flow: | 1 ml/min |
| Detector wavelength: | 225/275 nm. |
| Run time: | 40 min. |
| HPLC eluent: | n-Heptane/2-propanol/acetic acid (98:2:0.1) |

Chiral HPLC method 4 (decyl ester)

Conditions:

| | |
|---|---|
| Column: | Chiralpak AS 250*4.6 |
| Flow: | 0.9 ml/min |
| Detector wavelength: | 225/275 nm. |
| Run time: | 20 min. |
| HPLC eluent: | n-Heptane/2-propanol/acetic acid (97:3:0.1) |

Chiral HPLC method 5

Conditions:

| | |
|---|---|
| Column: | Chiralpak AS 250*4.6 |
| Flow: | 1 ml/min |
| Detector wavelength: | 225 nm. |
| Run time: | 40 min. |
| HPLC eluent: | n-Heptane/2-propanol/trifluoroacetic acid (96:4:0.1) |

Chiral Capillary Electrophoresis (CCE) Method 1

Conditions

HP 3D Capillary Electrophoresis 80.5/72.0 cm, 50 µm HP bubble capillary.

Electrolyte was 10/90 ACN/10 mM SB-β-CD (Advasep), 50 mM phosphate buffer pH 2.5 (HP).

Method

The reaction mixture diluted to approximately 0.04 mg/ml was injected (20 mbar in 3.0 seconds). The Rs was 1.7 and the migration times for the carboxylic acid product was 19.1 min and 19.4 min.

Chiral Capillary Electrophoresis (CCE) Method 2

Conditions

HP 3D Cappillary Electrophoresis 80.5/72.0 cm, 50 µm HP bubble capillary

Electrolyte was HS-β-CD (Regis)(2% w/v) and TM-β-CD (Sigma) (2% w/v) in 25 mM borate buffer buffer pH 9.3 (HP).

Method

The reaction mixture diluted approximately 25 times in borate buffer 5 mM pH9.3 for final concentration ca. 0.025 mg/ml–0.1 mg/ml injected (50 mbar in 4.0 seconds). The applied voltage 30 kV.

Preparaton of a Hydrolytic Enzyme Mixture from *Aspergillus oryzae*

*Aspergillus oryzae* IFO4177 was fermented using a fed-batch process with maltose/maltodextrin or glucose as the main carbon source. The batch medium contained: maltose/maltodextrin, ammonium sulphate, potassium-dihydrogenphosphate, yeast extract, beech xylan, MgSO4, 7H$_2$O, citric acid, potassium sulphate, trace metal solution and an anti-foam agent. All these components were used in concentrations all being within the range of 1–18 g/L final medium. The medium pH was considered a critical process parameter and kept at 4.5 throughout the fermentation. The feed consisted of maltoselmaltodextrin or glucose in the range of 280 g/L. 6.5 kg of batch medium was inoculated with 500 mL of seed culture. After 15–25 hours of batch fermentation the addition of feed was initiated using a feed addition rate of 15–25 g of feed per hour. This fed-batch state was continued for 100–160 hour of fermentation. Dissolved oxygen above 50% saturation was maintained by means of closed-loop control of the agitation rate. Aeration was kept at 1 volume air per volume batch medium per hour. A headspace pressure of 0.5 bar overpressure was maintained throughout the entire fermentation. After harvest of the broth, both biomass and un-dissolved matter was removed in a filtration step. The supernatant was concentrated by removal of water using ultrafiltration, evaporation or freeze drying.

Example 1

(2S)-2-Ethoxy-3-(4-hydroxyphenyl)propanoic acid/ Ethyl (2R)-2-ethoxy-3-(4-hydroxyphenyl) propanoate Ethyl (2RS) (+/−) 2-ethoxy-3-(4-hydroxyphenyl) propanoate (100 mg) was dissolved in water saturated 4-methyl-2-pentanone (18 ml) at room temperature. Immobilised *Mucor miehei* lipase immobilised on accurel EP 100 load: 187 klu/g (1 mg was added and the reaction mixture was shaken. The conversion of the racemic or enantiomerically enriched mixture of the ester was followed by the described isocratic HPLC procedures 1 and 2. Stirring was stopped at different times and ½ ml of the reaction mixture without enzyme was removed. Stirring was stopped after 4 hours and the reaction mixture stored at 3° C. for 18 hours. After this period of time the stirring of the reaction mixture was continued at room temperature.

Conversion of starting material (isocratic HPLC method 1):

| Time/hours | ½ | 1 | 1½ | 2 | 2½ | 3 | 4 | 5 | 7 | 9 |
|---|---|---|---|---|---|---|---|---|---|---|
| Product$_{acid}$ (%) | 10 | 18 | 25 | 31 | 36 | 40 | 46 | 58 | 61 | 64 |

The vial with the 4 and 9 hour sample was analysed by the CCE method:

Sample (4 h): Degree of conversion 51%; ee (ester): 69%.
Sample (9 h): Degree of conversion 79%; ee (ester): 81%.

Example 2

(2S)-2-Ethoxy-3-(4-hydroxyphenyl)propanoic acid/ Ethyl (2R)-2-ethoxy-3-(4-hydroxyphenyl) propanoate Ethyl (2RS) (+/−) 2-ethoxy-3-(4-hydroxyphenyl) propanoate (100 mg) was dissolved in water saturated 4-methyl-2-pentanone (18 ml) at room temperature. Immobilised *Humicola lanuginosa* lipase immobilised on accurel EP 100 load: 712 klu/g (0.5 mg) was added and the reaction mixture was shaken. The conversion of the racemic or enantiomerically enriched mixture of the ester was followed by the described isocratic HPLC procedures 1 and 2. The stirring was stopped at different times and ½ ml of the reaction mixture without enzyme was removed. The stirring was stopped after 4 hours and the reaction mixture stored at 3° C. for 18 hours. After this period of time the stirring of the reaction mixture was continued at room temperature.

Conversion of starting material (isocratic HPLC method 1):

| Time/hours | ½ | 1 | 1½ | 2 | 2½ | 3 | 4 | 5 | 7 | 9 |
|---|---|---|---|---|---|---|---|---|---|---|
| Product$_{acid}$ (%) | 1.4 | 2.9 | 4.5 | 6.5 | 8 | 10 | 13 | 27 | 31 | 36 |

The vial with the 9 hour sample was analysed by the CCE method 1:

Sample (9 h): Degree of conversion 57%; ee (ester): 29%.

Example 3

(2S)-2-Ethoxy-3-(4-hydroxyphenyl)propanoic acid/ 2-Ethoxyethyl (2R)-2-ethoxy-3-(4-hydroxyphenyl) propanoate Ethoxyethyl (2RS) (+/−) 2-ethoxy-3-(4-hydroxyphenyl) propanoate (0.5 ml of a solution containing 2 mg/ml in a phosphate, pH 7; 0.1 M, or acetate buffer, pH 5; 0.1 M) was added to the reaction vessel followed by an enzyme (0.5 ml enzyme solution). The reaction mixture was shaken at room temperature and analysed at different times (maximum 36 h). The reaction mixture was analysed without work up by the gradient HPLC method 1, chiral HPLC methods 2 and 5, and by the CCE method 1.

Conversion of starting material:

| Origin of Enzyme | Conc./ mg/ml | Buffer/ pH | Gradient HPLC | | | Chiral HPLC or chiral CE/ee |
|---|---|---|---|---|---|---|
| | | | 18 h | 24 h | 36 h | |
| *B. licheniformis*[a] | 5 | pH 7 | 68% | 71% | 84% | ee$_{acid}$ = 14 (24 h) ee$_{ester}$ = 19 (24 h) |
| *A. aculeatus*[b] | 6 | pH 5 | 27% | 33% | 47% | ee$_{acid}$ = 96 (36 h) ee$_{ester}$ = 78 (36 h) |
| *A. aculeatus*[c] | 2.5 | pH 5 | 57% | 58% | 61% | ee$_{acid}$ = 84 (18 h) ee$_{ester}$ ≈ 100 (18 h) |
| *A. oryzae*[d] | 1 | pH 7 | 20% | 25% | 36% | ee$_{acid}$ = 96 (36 h) ee$_{ester}$ = 58 (36 h) |

[a]Esperase ®;
[b]Protease 1 (or Aspergillopepsin II) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 327);
[c]Protease 2 (or Aspergillopepsin I) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 294);
[d]NpI protease (or Neutral proteinase I or Fungalysin) from *Aspergillus oryzae* expressed in *Aspergillus oryzae* also containing secreted enzymes from *Aspergillus oryzae* (EMBL ID = AC = AF099904; Handbook of Proteolytic Enzymes, Barrett, Rawlings, and Woessner Eds., 1998, Academic Press ref. 1 chap. 514).

Example 4

(2S)-2-Ethoxy-3-(4-hydroxyphenyl)propanoic acid/ Ethyl (2R)-2-ethoxy-3-(4-hydroxyphenyl) propanoate Ethyl (2RS) (+/−) 2-ethoxy-3-(4-hydroxyphenyl) propanoate (0.5 ml of a solution containing 2 mg/ml in a phosphate, pH 7; 0.1M, or acetate buffer, pH 5; 0.1 M) was added to the reaction vessel followed by an enzyme (0.5 ml enzyme solution). The reaction mixture was shaken at room temperature and analysed at different times (maximum 36 h). The reaction mixture was analysed without work up by the gradient HPLC method 1 and by chiral HPLC methods 2 and 5.

Conversion of starting material:

| Origin of Enzyme | Conc./ mg/ml | Buffer/ pH | Gradient HPLC | | | Chiral HPLC/ ee |
|---|---|---|---|---|---|---|
| | | | 3 h | 24 h | 36 h | |
| *Bacillus clausii*[a] | 2.5 | pH 7 | | 50% | 100% | ee$_{ester}$ = 72 (24 h) |
| *Bacillus clausii*[b] | 7 | pH 7 | 30% | 50% | 100% | ee$_{ester}$ = 91 (24 h) |
| *F. oxysporium*[c] | 7 | pH 7 | 35% | 50% | 50% | ee$_{ester}$ = 97 (24 h) |
| *A. aculeatus*[d] | 6 | pH 5[i] | | 50% | 50% | ee$_{ester}$ = 78 (24 h) |
| *A. aculeatus*[e] | 2.5 | pH 5[i] | 50% | 50% | 50% | ee$_{ester}$ ≈ 100 (24 h) |
| *A. aculeatus*[j] | 9 | pH 7 | | 49% | | ee$_{ester}$ ≈ 98% (24 h) |
| Bovine pancreas[f] | 2.5 | pH 7 | 85% | 100% | 100% | ee$_{ester}$ = 38 (3 h) |
| Bovine pancreas[g] | 5 | pH 7 | 50% | 100% | 100% | ee$_{ester}$ = 39 (3 h) |

-continued

| Origin of Enzyme | Conc./ mg/ml | Buffer/ pH | Gradient HPLC 3 h | 24 h | 36 h | Chiral HPLC/ee |
|---|---|---|---|---|---|---|
| A. oryzae[h] | 3 | pH 7 | 50% | 50% | 50% | ee$_{ester}$ = 97 (3 h) |

[a]Savinase from, *Bacillus clausii*;
[b]Kannase a variant of Savinase from *Bacillus clausii*;
[c]Trypsin like protease from *Fusarium oxysporum* expressed in *Aspergillus oryzae* also containing secreted enzymes from *Aspergillus oryzae* (Swissprot AC = P35049 and/or EMBL ID = AC = S63827, Handbook of Proteolytic Enzymes, Barrett, Rawlings, and Woessner Eds., 1998, Academic Press ref.1 chap. 3);
[d]Protease 1 (or Aspergillopepsin II) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 327);
[e]Protease 2 (or Aspergillopepsin I) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 294);
[f]α-chymotrypsin type II from bovine pancreas (SIGMA);
[g]α-chymotrypsin type VIII from bovine pancreas (SIGMA);
[h]Alp. protease (or oryzin) from *Aspergillus oryzae* expressed in *Aspergillus oryzae* also containing secreted enzymes from *Aspergillus oryzae* (Swissprot AC = P12547; Handbook of Proteolytic Enzymes, Barrett, Rawlings, and Woessner Eds., 1998, Academic Press ref.1 chap. 105);
[i]Acetate buffer, 0.1 M;
[j]Rheozyme, pectin methyl esterase from *Aspergillus aculeatus*.

Example 5

(2S)-2-Ethoxy-3-(4-hydroxyphenyl)propanoic acid/ Isopropyl (2R)-2-ethoxy-3-(4-hydroxyphenyl) propanoate Isopropyl (2RS) (+/−) 2-ethoxy-3-(4-hydroxyphenyl) propanoate (0.5 ml of a solution containing 2 mg/ml in a phosphate, pH 7; 0.1 M, or acetate buffer, pH 5; 0.1 M) was added to the reaction vessel followed by an enzyme (0.5 ml enzyme solution). The reaction mixture was shaken at room temperature and analysed at different times (maximum 28 h). The reaction mixture was analysed without work up by the gradient HPLC method 1, chiral HPLC methods 3 and 5, and by the CCE method 1.

Conversion of starting material:

| Origin of Enzyme | Conc./ mg/ml | Buffer/ pH | Gradient HPLC 6 h | 22 h | 28 h | Chiral HPLC and Chiral CE/ee |
|---|---|---|---|---|---|---|
| F. oxysporium[a] | 7 | pH 7 | 23% | 49% | 49% | ee$_{ester}$ = 86 (28 h) ee$_{acid}$ = 93 (28 h) |
| A. aculeatus[b] | 2.5 | pH 5[f] | 54% | 56% | 53% | ee$_{ester}$ ≈ 100 (22 h) ee$_{acid}$ = 97 (22 h) |
| A. oryzae[d] | 3 | pH 7 | 57% | 58% | 54% | ee$_{ester}$ ≈ 100 (28 h) ee$_{acid}$ = 86 (28 h) |

-continued

| Origin of Enzyme | Conc./ mg/ml | Buffer/ pH | Gradient HPLC 6 h | 22 h | 28 h | Chiral HPLC and Chiral CE/ee |
|---|---|---|---|---|---|---|
| H. insolens[e] | 5 | pH 7 | 11[g]% | 15[g]% | 24[g]% | ee$_{acid}$ = 79 (48 h) |

[a]Trpsin like protease from *Fusarium oxysporum* expressed in *Aspergillus oryzae* also containing secreted enzymes from *Aspergillus oryzae* (Swissprot AC = P35049 and/or EMBL ID = AC = S63827, Handbook of Proteolytic Enzymes, Barrett, Rawlings, and Woessner Eds., 1998, Academic Press ref.1 chap. 3);
[b]Protease 2 (or Aspergillopepsin I) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 294);
[d]Alp. protease (or oryzin) from *Aspergillus oryzae* expressed in *Aspergillus oryzae* also containing secreted enzymes from *Aspergillus oryzae* (Swissprot AC = P12547; Handbook of Proteolytic Enzymes, Barrett, Rawlings, and Woessner Eds., 1998, Academic Press ref.1 chap. 105);
[e]Cutinase from *H. insolens*;
[f]Acetate buffer, 0.1 M;
[g]Time interval 19, 26, 48 hours.

Example 6

(2S)-2-Ethoxy-3-(4-hydroxyphenyl)propanoic acid

Ethyl (2R/S) (+/−) 2-ethoxy-3-(4-hydroxyphenyl) propanoate (13 g) was added to an aqueous 0.1 M phosphate buffer pH 7 (2.6 μl). Protease 2A from *Aspergillus oryzae* (Fluka No: 82463; 0.51 units/mg) (7.9 g) was added and the mixture was stirred for 14 hours at room temperature. The conversion of ester to acid was followed by the described isocratic HPLC method 1. After stirring for 6 hours the reaction mixture was extracted 5× with ethyl acetate until no more ester could be detected in the aqueous phase (pH of the aqueous phase 6.8). A 4 M aqueous hydrogen chloride solution (200 ml) was added (pH of the aqueous phase 1) followed by tert-butyl-methylether (500 ml). The emulsion was filtered through hyflo and the two phases separated. The aqueous phase was extracted with tert-butyl-methylether (500 ml×3). The pooled organic phases were dried with Na$_2$SO$_4$ and evaporated to give 4.9 g of the title product (CCE method 1: ee=97%). δ(400 MHz; [$^2$H$_6$]DMSO) 1.04 (3H, t); 2.78 (2H, ddd), 3.38 (1H, dq); 3.49 (1H, dq); 3.90 (1H, m), 6.62 (2H, d); 7.0 (2H, d); 9.1 (1H, bs); 12.53 (1H, bs).

Conversion of starting material (isocratic HPLC method 1):

| Time/hours | 1 | 2 | 3 | 4 | 5 | 6 |
|---|---|---|---|---|---|---|
| Product$_{acid}$ (%) | 9 | 17 | 25 | 32 | 38 | 42 |

Example 7

(2R)-2-Ethoxy-3-(4-hydroxyphenyl)propanoic acid/ 2-Ethoxyethyl (2S)-2-Ethoxy-3-(4-hydroxyphenyl) propanoate Ethoxyethyl (2RS) 2-ethoxy-3-(4-hydroxyphenyl) propanoate (0.5 ml of a solution containing 2 mg/ml in a phosphate, pH 7, 0.1 M) was added followed by immobilised protease from *Pseudomonas putida* (L-aminopeptidase, available as Novozym 180 or SP 180 from Novo Nordisk) (5 mg) and phosphate buffer (0.1 M, pH 7, 0.5 ml); The reaction mixture was shaken at room temperature and analysed at different times (maximum 36 h). The reaction mixture was analysed without work up by the gradient HPLC method 1 and by the chiral HPLC method.

Conversion of starting material:

|  | Time/hours | | |
| --- | --- | --- | --- |
|  | 18 | 24 | 36 |
| Product$_{acid}$ (%) | 49 | 36 | 46 |
| Product$_{Acid}$ (ee) | 37 | 43 | 40 |

Example 8

(2R)-2-Ethoxy-3-(4-hydroxyphenyl)propanoic acid/ Isopropyl (2S)-2-ethoxy-3-(4-hydroxyphenyl) propanoate Isopropyl (2RS) (+/−) 2-ethoxy-3-(4-hydroxyphenyl) propanoate (0.5 ml of a solution containing 2 mg/ml in a phosphate buffer, 0.1 M, pH 7) was added followed by α-chymotrypsin type II from bovine pancreas (SIGMA) (2.5 mg in a phosphate buffer. 0.1M, pH 7, 0.5 ml). The reaction mixture was shaken at room temperature and analysed at different times (maximum 28 h). The reaction mixtures were analysed by the gradient HPLC method 1 and by the chiral HPLC method.

Conversion of starting material:

|  | Time/hours | | |
| --- | --- | --- | --- |
|  | 6 | 22 | 28 |
| Product$_{Acid}$ (%) | 22 | 53 | 52 |
| Product$_{ester}$ (ee) |  | 44 | 52 |
| Product$_{acid}$ (ee) |  | 65 | 58 |

Example 9

(2S)-2-Ethoxy-3-(4-hydroxyphenyl)propanoic acid/ Ethyl (2R)-2-Ethoxy-3-(4-hydroxyphenyl) propanoate Ethyl (2RS) (+/−) 2-ethoxy-3-(4-hydroxyphenyl) propanoate 0.4 ml of a solution containing 6.25 mg/ml in acetate buffer (0.1 M, pH 5 with acetonitrile 12.5 vol. % added to the buffer) was added followed by a sample of Protease 2 (or Aspergillopepsin I) from *Aspergillus aculeatus* expressed in *Aspergillus oryzae* also containing secreted enzymes from *Aspergillus oryzae* (WO95/02044; *Handbook of Proteolytic Enzymes*, Barrett, Rawlings, and Woessner Eds., 1998, Academic Press ref.1 chap. 294) (0.1 ml of a solution containing 5 mg/ml) in an acetate buffer (0.1 M; pH=5). The reaction mixture was shaken at room temperature and analysed at different times (maximum 24 h). The reaction mixture was analysed by the gradient HPLC method 1 and by the chiral HPLC method 1.

Conversion of starting material:

|  | Time/hours | | |
| --- | --- | --- | --- |
|  | 5 | 8 | 24 |
| Product$_{acid}$ (%) | 35 | 43 | 50 |
| Product$_{Acid}$ (ee) | ≧95 | ≧95 | ≧95 |
| Product$_{Ester}$ (ee) | 52 | 74 | ≈100 |

Example 10 n-Decyl (2S)-2-Ethoxy-3-(4-hydroxyphenyl) propanoate/Ethyl (2R)-2-Ethoxy-3-(4-hydroxyphenyl)propanoate Ethyl (2RS) (+/−) 2-ethoxy-3-(4-hydroxyphenyl) propanoate (9 mg) was added to a solution containing: Immobilised *Mucor miehei* lipase immobilised on accurel EP 100 load :187 klu/g (18 mg), n-decanol 14 μl, heptane 0.9 ml and 4 Å molecular sieves. The reaction mixture was shaken at room temperature and analysed at different times (maximum 7 h). The reaction mixtures were analysed by the gradient HPLC method 2 and by the chiral HPLC method 4.

Conversion of starting material:

|  | Time/hours | |
| --- | --- | --- |
|  | 3 | 7 |
| Product$_{acid}$ (%) | 46 | 46 |
| Decyl ester (ee) | 86 | 68 |
| Ethyl ester (ee) | 70 | 67 |

Example 11

Esterification of (2RS)-2-Ethoxy-3-(4-hydroxyphenyl)propanoic acid with n-alkyl alcohols (2RS) (+/−) 2-ethoxy-3-(4-hydroxyphenyl)propanoic acid (100 mg) and the respective n-alkyl alcohol (1.2 eq.) dissolved in 1 ml tert-butyl methyl ether (TMBE) were shaken together with 10 mg of Lipozyme IM (immobilised *Mucor miehei* lipase commercially available from Novo Nordisk) at 25° C. (40° C. for MeOH). The reaction mixture was analysed at different times by the chiral CCE method 2.

Yield and ee of the respective ester after 48 h and 144 h:

| Alcohol | Product$_{ester}$ 48 h (%) | (ee)$_{ester}$ 48 h (%) | (ee)$_{acid}$ 48 h (%) | Product$_{ester}$ 144 h (%) | (ee)$_{ester}$ 144 h (%) | (ee)$_{acid}$ 144 h (%) |
| --- | --- | --- | --- | --- | --- | --- |
| Methanol | 33 | n.d. | 40 | n.d. | n.d. | n.d. |
| Ethanol | 28 | 89 | 34 | 40 | 78 | 48 |
| 1-Propanol | 31 | 86 | 32 | 43 | 64 | 61 |
| 1-Butanol | 18 | 89 | 14 | 38 | 78 | 72 |

-continued

| Alcohol | Product$_{ester}$ 48 h (%) | (ee)$_{ester}$ 48 h (%) | (ee)$_{acid}$ 48 h (%) | Product$_{ester}$ 144 h (%) | (ee)$_{ester}$ 144 h (%) | (ee)$_{acid}$ 144 h (%) |
|---|---|---|---|---|---|---|
| 1-Pentanol | 20 | n.d. | 18 | 39 | n.d. | 69 |
| 1-Hexanol | 15 | n.d. | 20 | 40 | n.d. | 69 |
| 1-Heptanol | 20 | 77 | 20 | 43 | 61 | 70 |
| 1-Octanol | 19 | 91 | 22 | 45 | 49 | 66 |
| 1-Dodecanol | n.d. | 18 | 20 | 43 | 44 | 64 |
| 3-Methyl-1-butanol | 24 | 30 | 20 | 42 | 49 | 63 |
| 4-Methyl-1-pentanol | 18 | 22 | 14 | 42 | n.d. | 68 |
| 2-Propanol | n.d. | n.d. | n.d. | 6 | >99 | 6 |

Example 12

(2S)-2-Ethoxy-3-(4-hydroxyphenyl)propanoic acid/
Ethyl (2R)-2-Ethoxy-3-(4-hydroxyphenyl)
propanoate Ethyl (2RS) (+/−) 2-ethoxy-3-(4-hydroxyphenyl) propanoate (0.5 g) was shaken with 60 mg of the lyophilised hydrolytic enzyme mixture from *Aspergillus oryzae* in 1 ml 1M phosphate buffer (pH=7) with organic co-solvents (according to the table below) at 27° C. The reaction mixture was poured into 20 ml MeOH after 4 h to stop the enzymatic reactions followed by analysis by the chiral CCE method 2.

| Co-solvent | Product$_{acid}$ (%) | (ee)$_{acid}$ (%) |
|---|---|---|
| Acetone/0.1 ml | 37 | 93 |
| Acetone/0.3 ml | 31 | 94 |
| THF/0.1 ml | 36 | 94 |
| THF/0.2 ml | 31 | 93 |
| THF/0.3 ml | 21 | 91 |
| 2-Propanol/0.1 ml | 36 | 97 |
| 2-Propanol/0.3 ml | 27 | 93 |
| Ethanol/0.1 ml | 35 | 96 |
| Ethanol/0.2 ml | 32 | 96 |
| Ethanol/0.3 ml | 22 | 93 |

Example 13

Esterification of enantiomerically enriched (2S)-2-Ethoxy-3-(4-hydroxyphenyl)propanoic acid with ethanol Enantiomerically enriched (2S) (+/−) 2-ethoxy-3-(4-hydroxyphenyl)propanoic acid, and ethanol (1.5–2 eq.) dissolved in tert-butyl methyl ether (4–10 ml /g of acid) were stirred together with 10–30 wt. % $_{/tacid}$ of Lipozyme IM (immobilised *Mucor miehei* lipase commercially available from Novo Nordisk) at ambient temperature or at reflux. The reaction mixtures were analysed by the chiral CCE method 2 when the conversions (determined by gradient HPLC method 3) reported in the table below were reached.

Yield and ee of the starting acid and the final ethyl ester.

| Entry | (ee)$_{acid}$ | Product$_{ester}$ (%) | Product$_{ester}$ (ee$_%$) |
|---|---|---|---|
| 1 | 94 | 86 | 98 |
| 2 | 96 | 93 | 99 |
| 3 | 99 | 93 | >99 |
| 4 | 93 | 85 | 99 |

-continued

| Entry | (ee)$_{acid}$ | Product$_{ester}$ (%) | Product$_{ester}$ (ee$_%$) |
|---|---|---|---|
| 5 | 79 | 76 | 97 |
| 6 | 89 | 93 | 98 |
| 7 | 91 | 88 | 99 |
| 8 | 96 | 92 | 99 |

Example 14

Ethyl (2R)-2-Ethoxy-3-(4-hydroxyphenyl)
propanoate

Enantiomerically enriched (ee R$_{enantiomer}$=60%) ethyl 2-ethoxy-3-(4-hydroxyphenyl)propanoate (5.2 g) was dissolved in 30 ml acetone and added to an aqueous 0.1 M phosphate buffer pH 7 (1.0 l). Protease 2A from *Aspergillus oryzae* (Fluka No: 82463; 0.51 units/mg) (13 g) was added and the mixture was stirred for 3 days at room temperature. The reaction mixture was extracted 4× with 200 ml TBME. After drying of the combined organic phases over Na$_2$SO$_4$ and evaporation of the TBME, 4.3 g of ethyl (2R)-2-Ethoxy-3-(4-hydroxyphenyl)propanoate was obtained as an oil (CCE method 2: ee=100%).

Conversion of starting material (isocratic HPLC method 1):

| | Time/hours | |
|---|---|---|
| | 8 | 72 |
| Product$_{acid}$ (%) | 14 | 25 |

Example 15

(2S)-2-Ethoxy-3-(4-hydroxyphenyl)propanoic acid/
Ethyl (2R)-2-Ethoxy-3-(4-hydroxyphenyl)
propanoate Ethyl (2R/S) (+/−) 2-ethoxy-3-(4-hydroxyphenyl) propanoate (5 g) was added to an aqueous 0.1 M phosphate buffer pH 7 (10 ml). Pectinex Ultra SP-L (Novo Nordisk) (15 ml) was added and the mixture was stirred for 44 hours at room temperature. During that time, the pH of the reaction mixture was kept constant at pH=7 by addition of NaOH. Most of the water was evaporated in vacuo. Methanol was added to the remaining slurry in order to stop the hydrolysis. The precipitate, which formed was filtered off and the methanol was evaporated in vacuo. The remaining oil was dissolved in water followed by extraction of unreacted ester with TMBE (CCE method 2: $ee_{ester}$=100%). The water phase was acidified to pH=3 and the acid extracted with TMBE. After drying over $Na_2SO_4$ and evaporation of the TMBE, 1.7 g (2S)-2-Ethoxy-3-(4-hydroxyphenyl)propanoic acid was obtained as an oil, which crystallized on standing (CCE method 2: $ee_{acid}$=98%).

Example 16

(2S)-2-Ethoxy-3-(4-hydroxyphenyl)propanoic acid/ Ethyl (2R)-2-Ethoxy-3-(4-hydroxyphenyl) propanoate Ethyl (2R/S) (+/−) 2-ethoxy-3-(4-hydroxyphenyl)propanoate (5 g) was added to an aqueous 0.1 M phosphate buffer pH 7 (10 ml). 100 mg of the lyophilised hydrolytic enzyme mixture from *Aspergillus oryzae* was added and the mixture was stirred for 18 hours at room temperature. During that time, the pH of the reaction mixture was kept constant at pH=6–8 by addition of NaOH. Most of the water was evaporated in vacuo. Methanol was added to the remaining slurry in order to stop the hydrolysis. The precipitate, which formed was filtered off and the methanol was evaporated in vacuo. The remaining oil was dissolved in water followed by extraction of unreacted ester with TMBE (CCE method 2: $ee_{ester}$=87%). The water phase was acidified to pH=3 and the acid extracted with TMBE. After drying over $Na_2SO_4$ and evaporation of the TMBE, 1.8 g (2S)-2-Ethoxy-3-(4-hydroxyphenyl)propanoic acid was obtained as an oil, which crystallized on standing (m.p.=105° C., CCE method 2: $ee_{acid}$=>99%).

Example 17 n-Decyl (2S)-2-Ethoxy-3-(4-hydroxyphenyl) propanoate/Ethyl (2R)-2-Ethoxy-3-(4-hydroxyphenyl)propanoate To ethyl (2RS) (+/−) 2-ethoxy-3-(4-hydroxyphenyl)propanoate (5 mg) in solution in heptane (dried on 4 Å molecular sieves) (1 ml), triethylamine (0.4 μl) and n-decanol (8 μl), were added 4 Å molecular sieves and *Rhizopus arrhizus* lipase (Fluka 62305; 2.2 U/g) (20 mg). The reaction mixture was shaken at room temperature and analysed at different times. The reaction mixtures were analysed by the gradient HPLC method 2 and by the chiral HPLC method 4.

Conversion of starting material:

|  | Time/hours | |
| --- | --- | --- |
|  | 24 | 72 |
| Product (decane ester) (%) | 29 | 47 |
| Decane ester (% ee) |  | 47 |

Example 18 n-Decyl (2S)-2-ethoxy-3-(4-hydroxyphenyl) propanoate acid/Ethyl (2R)-2-ethoxy-3-(4-hydroxyphenyl)propanoate To ethyl (2RS) (+/−) 2-ethoxy-3-(4-hydroxyphenyl)propanoate (5 mg) in solution in heptane (dried on 4 Å molecular sieves) (0.5 ml), triethylamine (0.4 μl) and n-decanol (8 μl) were added 4 Å molecular sieves and *Aspergillus niger* lipase (Fluka 62294; 1 U/mg) (40 mg). The reaction mixture was shaken at room temperature and analysed at different times. The reaction mixtures were analysed by the gradient HPLC method 2 and by the chiral HPLC method 4.

Conversion of starting material:

|  | Time/hours | |
| --- | --- | --- |
|  | 24 | 72 |
| Decyl ester (%) | 31 | 47 |
| % $ee_{decyl\ ester}$ |  | 56 |

Example 19

(2S)-2-Ethoxy-3-(4-hydroxyphenyl)propanoic acid/ Ethyl (2R)-2-Ethoxy-3-(4-hydroxyphenyl) propanoate To ethyl (2RS) (+/−) 2-ethoxy-3-(4-hydroxyphenyl)propanoate (0.5 ml of a solution containing 1 mg/ml in a phosphate or citrate-phosphate 0.1 M buffer) was added the enzyme (amount indicated below). The reaction mixture was shaken at room temperature and analysed at different times. The reaction mixture was analysed by the gradient HPLC method 1 and by chiral HPLC.

Conversion of starting material:

| Enzyme | Enzyme amount | Buffer/ pH | Reaction time | % product | $ee_{product}$ |
| --- | --- | --- | --- | --- | --- |
| Proteinase 6[a] | 0.5 mg | pH 7[h] | 96 h | 46 | 47 |
| Flavourzyme ®[b] | 250 μl | pH 7[i] | 23 h | 39 | 50 |
| Pectinex BE 3L ®[c] | 100 μl | pH 5[i] | 5 mn | 47 | 95 |
| Kojizyme 500 MG ®[d] | 10 mg | pH 6[i] | 50 mn | 45 | 98 |
| Ferulic acid esterase[e] | 200 μl | pH 7[i] | 23 h | 49 | 98 |
| Acetyl xylan Esterase[f] | 100 μl | pH 7[h] | 26 h | 47 | 99 |
| Pectinex Ultra SP-L ®[g] | 250 μl | pH 7[h] | 15 mn | 46 | 99 |

[a]Proteinase 6 from Aspergillus sp. (Fluka 82539);
[b]Flavourzyme from *A. oryzae* (Novo Nordisk)
[c]Pectinex BE 3L ® from *Aspergillus niger* (Nova Nordisk);
[d]Kojizyme 500 MG ® from *Aspergillus oryzae* (Nova Nordisk);
[e]Ferulic acid esterase from *Aspergillus oryzae* (0.5 mg/ml);
[f]Acetyl xylan esterase from *Aspergillus aculeatus* (2 mg/ml);
[g]Pectinex Ultra SP-L from *Aspergillus aculeatus* (Nova Nordisk);
[h]Phosphate buffer, 0.1 M;
[i]Phosphate-citrate buffer 0.1 M.

Example 20

(2S)-2-Ethoxy-3-(4-hydroxyphenyl)propanoic acid/ Hexyl (2R)-2-Ethoxy-3-(4-hydroxyphenyl) propanoate To hexyl (2RS) (+/−) 2-ethoxy-3-(4-hydroxyphenyl)propanoate (0.5 ml of a solution containing 2 mg/ml in a phosphate, pH 7; 0.1M, or acetate buffer, pH 5; 0.1 M) was added the enzyme (0.5 ml enzyme solution). The reaction mixture was shaken at room temperature and analysed at different times (maximum 30 h). The reaction mixture was analysed by the gradient HPLC method 1, and the chiral CE method 1.

Conversion of starting material:

| Origin of Enzyme | Conc./ mg/ml | Buffer/ pH | % Hydrolysis | | | % ee_acid |
|---|---|---|---|---|---|---|
| | | | 6 h | 24 h | 30 h | |
| B. clausii[a] | 7 | pH7[e] | 52% | | | 20 (6 h) |
| B. licheniformis[b] | 5 | pH7[e] | 14% | 45% | | 20 (24 h) |
| A. aculeatus[c] | 2 | pH5[f] | 42% | | | 97 (6 h) |
| A. oryzae[d] | 1 | pH7[e] | 12% | 32% | 48% | 89 (30 h) |

[a]Kannase ®, a variant of Savinase from *Bacillus clausii*;
[b]Esperase ® from *B. licheniformis*;
[c]Protease 2 (or Aspergillopepsin I) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 294);
[d]Npl protease (or Neutral proteinase I or Fungalysin) from *Aspergillus oryzae* expressed in *Aspergillus oryzae* also containing secreted enzymes from *Aspergillus oryzae* (EMBL ID = AC = AF099904; Handbook of Proteolytic Enzymes, Barrett, Rawlings, and Woessner Eds., 1998, Academic Press ref.1 chap. 514);
[e]Phosphate buffer 0.1 M; [f]Acetate buffer 0.1 M Example 21

(2S)-2-Ethoxy-3-(4-hydroxyphenyl)propanoic acid/
Ethyl (2R)-2-Ethoxy-3-(4-hydroxyphenyl)
propanoate The enzyme (100 μl)[a] was added to ethyl (2RS) (+/−) 2-ethoxy-3-(4-hydroxyphenyl)propanoate (2.5 mg in solution in acetate buffer 0.1M pH 5 (350 μl) and an organic co-solvent according to the table below) (50 μl)). The reaction mixture was shaken at room temperature and analysed at different times. The reaction mixture was analysed by the gradient HPLC method 1 and by chiral CE method 1.

[a]Protease 2 (or Aspergillopepsin I) from *Aspergillus aculeatus* expressed in *Aspergillus oryzae* also containing secreted enzymes from *Aspergillus oryzae* (WO95/02044; Handbook of Proteolytic Enzymes, Barrett, Rawlings, and Woessner Eds., 1998, Academic Press ref.1 chap. 294) (1 mg/ml)

Conversion of starting material:

| Co-solvent | % hydrolysis | | | | % ee_acid |
|---|---|---|---|---|---|
| | 1 h 30 | 2 h 30 | 4 h | 5 h | |
| t-Butanol | 27 | 36 | 43 | 46 | 99 (5 h) |
| Acetone | 28 | 37 | 44 | 47 | 99 (5 h) |
| DMF | 24 | 33 | 40 | 44 | 99 (5 h) |
| DMSO | 35 | 42 | 47 | 49 | 99 (5 h) |

Example 22

(2S)-2-Ethoxy-3-(4-hydroxyphenyl)-propanoic acid/
Ethyl (2R)-2-Ethoxy-3-(4-hydroxyphenyl)-
propanoate To ethyl (2RS) (+/−) 2-ethoxy-3-(4-hydroxyphenyl)-propanoate (0.25 ml of a solution containing 2 mg/ml in phosphate 0.1M buffer pH 7) was added the enzyme (amount indicated below) diluted in phosphate buffer 0.1M pH 7 (buffer volume such as total reaction mixture volume was 0.5 ml). The reaction mixture was shaken at room temperature and analysed at different times. The reaction mixture was analysed by the gradient HPLC method 1 and by the chiral CE method 2.

Conversion of starting material:

| Enzyme | Enzyme amount | Reaction time | % product | ee_product |
|---|---|---|---|---|
| Pectinex Smash ®[a] | 10 μl | 1 h 15 | 46 | 99% |
| Pectinex AFP L-2 ®[b] | 10 μl | 1 h | 46 | 98% |
| Novozyme 188 ®[c] | 50 μl | 37 mn | 47 | 98% |
| Shearzyme 500L ®[d] | 50 μl | 37 mn | 42 | 99% |

[a]Pectinex Smash ® (Novo Nordisk);
[b]Pectinex AFP L-2 ® from *Aspergillus niger* and *Aspergillus aculeatus* (Nova Nordisk);
[c]Novozyme 188 ® from *Aspergillus niger* (Novo Nordisk)
[d]Shearzyme 500L from *Aspergillus oryzae* (Novo Nordisk)

Example 23

(2S)-2-Ethoxy-3-(4-hydroxyphenyl)-propanoic acid/
Isopropyl (2R)-2-Ethoxy-3-(4-hydroxyphenyl)-
propanoate To isopropyl (2RS) (+/−) 2-ethoxy-3-(4-hydroxyphenyl)-propanoate (0.25 ml of a solution containing 2 mg/ml in phosphate buffer 0.1 M pH 7 and acetonitrile 10% (v/v)) was added the enzyme (amount indicated below) diluted in phosphate buffer 0.1M pH 7 (buffer volume such as total reaction mixture volume was 0.5 ml). The reaction mixture was shaken at room temperature and analysed at different times. The reaction mixture was analysed by the gradient HPLC method 1, and the chiral CE method 2.

Conversion of starting material:

| Enzyme | Enzyme amount | Reaction time | % product | ee_product |
|---|---|---|---|---|
| Pectinex Smash ®[a] | 10 μl | 1 h 15 | 46 | ≈100% |
| Pectinex AFP L-2 ®[b] | 10 μl | 1 h 30 | 46 | 99% |
| Novozyme 188 ®[c] | 25 μl | 1 h 10 | 48 | 98% |
| Shearzyme 500L ®[d] | 25 μl | 1 h 30 | 48 | 99% |

[a]Pectinex Smash ® (Novo Nordisk);
[b]Pectinex AFP L-2 ® from *Aspergillus niger* and *Aspergillus aculeatus* (Novo Nordisk);
[c]Novozyme 188 ® from *Aspergillus niger* (Novo Nordisk)
[d]Shearzyme 500L ® from *Aspergillus oryzae* (Novo Nordisk)

Example 24

(2S)-2-Ethoxy-3-(4-hydroxyphenyl)-propanoic acid/
Ethoxyethyl (2R)-2-Ethoxy-3-(4-hydroxyphenyl)-
propanoate To ethoxyethyl (2RS) (+/−) 2-ethoxy-3-(4-hydroxyphenyl)-propanoate (0.25 ml of a solution containing 2 mg/ml in phosphate buffer 0.1M pH 7) was added the enzyme (amount indicated below) diluted in phosphate buffer 0.1M pH 7 (buffer volume such as total reaction mixture volume was 0.5 ml). The reaction mixture was shaken at room temperature and analysed at different times. The reaction mixture was analysed by the gradient HPLC method 1, and the chiral CE method 2.

Conversion of starting material:

| Enzyme | Enzyme amount | Reaction time | % product | ee$_{product}$ |
|---|---|---|---|---|
| Pectinex Smash ®[a] | 10 µl | 45 mn | 43 | 98% |
| Pectinex AFP L-2 ®[b] | 10 µl | 45 mn | 44 | 98% |
| Novozyme 188 ®[c] | 25 µl | 30 mn | 47 | 96% |
| Shearzyme 500L ®[d] | 25 µl | 30 mn | 47 | 99% |

[a]Pectinex Smash ® (Novo Nordisk);
[b]Pectinex AFP L-2 ® from *Aspergillus niger* and *Aspergillus aculeatus* (Novo Nordisk);
[c]Novozyme 188 ® from *Aspergillus niger* (Novo Nordisk)
[d]Shearzyme 500L ® from *Aspergillus oryzae* (Novo Nordisk)

Example 25

(2S)-2-Ethoxy-3-(4-hydroxyphenyl)-propanoic acid/ Hexyl (2R)-2-Ethoxy-3-(4-hydroxyphenyl)-propanoate To hexyl (2RS) (+/−) 2-ethoxy-3-(4-hydroxyphenyl)-propanoate (0.25 ml of a suspension containing 2 mg/ml in phosphate buffer 0.1M pH 7 and acetonitrile (amount indicated below)) was added the enzyme (amount indicated below) diluted in phosphate buffer 0.1M pH 7 (buffer volume such as total reaction mixture volume was 0.5 ml). The reaction mixture was shaken at room temperature and analysed at different times. The reaction mixture was analysed by the gradient HPLC method 1, and the chiral CE method 2.

Conversion of starting material:

| Enzyme | Enzyme amount | Aceto-nitrile[e] | Reaction time | % product | ee$_{product}$ |
|---|---|---|---|---|---|
| Pectinex AFP L-2 ®[b] | 10 µl | 5% | 1 h | ≈47% | 99% |
| Novozyme 188 ®[c] | 25 µl | 15% | 1 h | ≈41% | ≈100% |
| Shearzyme 500L ®[d] | 25 µl | 15% | 1 h 30 | ≈46% | 99% |

[a]Pectinex Smash ® (Novo Nordisk);
[b]Pectinex AFP L-2 ® from *Aspergillus niger* and *Aspergillus aculeatus* (Novo Nordisk);
[c]Novozyme 188 ® from *Aspergillus niger* (Novo Nordisk)
[d]Shearzyme 500L ® from *Aspergillus oryzae* (Novo Nordisk);
[e]Percentage (v/v) of reaction mixture volume

Example 26 n-Hexyl (2R)-2-Ethoxy-3-(4-hydroxyphenyl) propanoate/Ethyl (2S)-2-Ethoxy-3-(4-hydroxyphenyl)propanoate To a solution of ethyl (2RS) (+/−) 2-ethoxy-3-(4-hydroxyphenyl)propanoate in t-butyl ethyl ether (dried on 3 Å molecular sieve) (10 mg/ml) was added n-hexanol (2 equivalents), triethylamine (dried on 3 Å molecular sieve) (14 mol %), 4 Å molecular sieve, and *Mucor miehei* lipase Lipozyme IM (from Novo Nordisk) (20 mg). The reaction mixture was shaken at room temperature and analysed at different times. The reaction mixture was analysed by the gradient HPLC method 1 and by the chiral CE method 2.

Conversion of starting material:

| Time/hours | 1 | 3 |
|---|---|---|
| Product$_{hexyl\ ester}$ (%) | 37 | 51 |
| Ethyl ester (% ee) | 57 | 74 |

Example 27

Alkyl (2R)-2-Ethoxy-3-(4-hydroxyphenyl) propanoate/Ethyl (2S)-2-Ethoxy-3-(4-hydroxyphenyl)propanoate To a solution of ethyl (2RS) (+/−) 2-ethoxy-3-(4-hydroxyphenyl)propanoate in t-butyl ethyl ether (dried on 3 Å molecular sieve) (10 mg/ml) was added the alkanol (2 equivalents), triethylamine (dried on 3 Å molecular sieve) (14 mol %), 4 Å molecular sieve, and *Mucor miehei* lipase Lipozyme IM (from Novo Nordisk) (20 mg). The reaction mixture was shaken at room temperature and analysed at different times. The reaction mixture was analysed by the gradient HPLC method 1 and by the chiral CE method 2.

Conversion of starting material:

| Alkanol | Reaction time | % trans-esterification | % ee$_{Ethyl\ ester}$ | % ee$_{Product\ ester}$ |
|---|---|---|---|---|
| n-butanol | 1 h 30 | 36% | 56% | 71% |
|  | 5 h 30 | 56% | 71% | 45% |
| 3-methyl 1-butanol | 3 h | 38% | 67% | nd |
|  | 5 h | 53% | 77% | nd |

Example 28 n-Decyl (2S)-2-Ethoxy-3-(4-hydroxyphenyl) propanoate/Ethyl (2R)-2-Ethoxy-3-(4-hydroxyphenyl)propanoate Ethyl (2RS) (+/−) 2-ethoxy-3-(4-hydroxyphenyl) propanoate (5 mg) was added to a solution containing *Mucor miehei* lipase Lipozym IM (immobilised *Mucor miehei* lipase commercially available from Novo Nordisk) (10 mg), n-decanol 8 µl, heptane 0.5 ml and 4 Å molecular sieves. The reaction mixture was shaken at room temperature and analysed at different times. The reaction mixtures were analysed by the gradient HPLC method 2 and by the chiral HPLC method.

Conversion of starting material:

| Time/hours | 2 h |
|---|---|
| Product$_{decyl\ ester}$ (%) | 46 |
| Decyl ester (ee) | 87 |
| Ethyl ester (ee) | 78 |

Example 29

Esterification of (2R,S)-2-Ethoxy-3-(4-hydroxyphenyl)propanoic acid with alcohols Racemic (2R,S) (+/−) 2-ethoxy-3-(4-hydroxyphenyl) propanoic acid (200 mg), and different alcohols (1.2 eq.)

dissolved in tert-butyl methyl ether (2 ml) were shaken together with 20 mg of Lipozyme IM (immobilised *Mucor miehei* lipase commercially available from Novo Nordisk) at 25° C. The reaction mixtures were analysed after 243 hours by the chiral CCE method 2 and the gradient HPLC-method 3.

Conversion and ee of the starting acid

| Alcohol | Remaining R-acid (ee %) | Product$_{ester}$ (%) |
|---|---|---|
| 4,4,4,-Trifluorobutanol | 40 | 39 |
| 2-(Methylmercapto) ethanol | 28 | 36 |
| 5-Hexen-1-ol | 64 | 23 |
| 3-Hydroxypropionitrile | 14 | 22 |
| 3,3-Dimethyl-1-butanol | 24 | 14 |
| Diethyleneglycolmonochlorhydrine | 10 | 12 |
| 3-Chlor-1-propanol | 44 | 37 |
| 2-Penten-4-yl-1-ol (E/Z mixture) | 20 | 19 |
| Citronellol | 66 | 63* |
| 3-Cyclohexyl-1-propnanol | 66 | 60* |
| 3-Phenylpropylalcohol | 60 | 58* |
| 3-(4-Hydroxyphenyl)propanol | 66 | 37 |

*: Data from CE-measurement

Example 30

(2S)-2-Ethoxy-3-(4-hydroxyphenyl)propanoic acid/ Ethyl (2R)-2-Ethoxy-3-(4-hydroxyphenyl)propanoate To ethyl (2RS) (+/−) 2-ethoxy-3-(4-hydroxyphenyl)-propanoate (2.5 mg) in citrate-phosphate buffer 0.1M (400 μl) (pH as indicated below) was added the Protease 2 (or Aspergillopepsin I) from *Aspergillus aculeatus* expressed in *Aspergillus oryzae* also containing secreted enzymes from *Aspergillus oryzae* (WO95/02044; *Handbook of Proteolytic Enzymes*, Barrett, Rawlings, and Woessner Eds., 1998, Academic Press ref.1 chap. 294) (100 μl, 1 mg protein/ml final concentration). The reaction mixture was shaken at room temperature and analysed at different times. The reaction mixture was analysed by the gradient HPLC method 1 and by the chiral HPLC method 5.

| | pH5 | | pH6 | | pH7 | |
|---|---|---|---|---|---|---|
| Time | % product | % ee product | % product | % ee product | % product | % ee product |
| 3 h | 40 | 99 | 41 | 99 | 41 | 98 |
| 3 h 30 | 42 | 99 | 43 | 99 | 43 | 99 |
| 4 h | 44 | 99 | 45 | 98 | 45 | 99 |
| 4 h 30 | 45 | 99 | 46 | 99 | 46 | 99 |

Example 31

(2S)-2-Ethoxy-3-(4-hydroxyphenyl)propanoic acid/ Ethyl (2R)-2-Ethoxy-3-(4-hydroxyphenyl)propanoate To ethyl (2RS) (+/−) 2-ethoxy-3-(4-hydroxyphenyl) propanoate (2.5 mg) in citrate-phosphate buffer 0.1M pH 5 (400 μl) was added the Protease 2 (or Aspergillopepsin I) from *Aspergillus aculeatus* expressed in *Aspergillus oryzae* also containing secreted enzymes from *Aspergillus oryzae* (WO95/02044; *Handbook of Proteolytic Enzymes*, Barrett, Rawlings, and Woessner Eds., 1998, Academic Press ref.1 chap. 294) (100 μl, 1 mg protein/ml final concentration). The reaction mixture was shaken at the temperatures indicated below and analysed at different times. The reaction mixture was analysed by the gradient HPLC method 1 and by the chiral HPLC method 5.

| | 20° C. | | 30° C. | |
|---|---|---|---|---|
| Time | % product | % ee product | % product | % ee product |
| 3 h | n.d | n.d | 46 | 99 |
| 3 h 30 | 42 | 99 | 47 | 99 |
| 4 h | 43 | 99 | 49 | 99 |
| 4 h 30 | 45 | 99 | 48 | 98 |
| 5 h | 46 | 99 | n.d | n.d |
| 5 h 30 | 48 | 99 | n.d | n.d |
| 6 h | 48 | 99 | n.d | n.d |

Example 32 n-Decyl (2S)-2-Ethoxy-3-(4-hydroxyphenyl)propanoate/Ethyl (2R)-2-Ethoxy-3-(4-hydroxyphenyl)propanoate Ethyl (2RS) (+/−) 2-ethoxy-3-(4-hydroxyphenyl) propanoate (5 mg) was added to a solution containing *Mucor miehei* lipase Lipozym IM (immobilised *Mucor miehei* lipase commercially available from Novo Nordisk) (10 mg), n-decanol 8 μl, heptane 0.5 ml and 4 Å molecular sieves. The reaction mixture was shaken at room temperature and analysed at different times. The reaction mixtures were analysed by the gradient HPLC method 2 and by the chiral HPLC method 4.

Conversion of starting material:

| Time/hours | 2 h |
|---|---|
| Product$_{acid}$ (%) | 46 |
| Decyl ester (ee) | 87 |
| Ethyl ester (ee) | 78 |

What is claimed is:

1. A process by which one of the two enantiomers of a racemic or enantiomerically enriched substrate of formula (I) is converted to formula (III) by a higher rate than the other enantiomer to give a reaction mixture from which the product mixtures (II) and (III) can be separated, comprising:

hydrolyzing one of the two enantiomeric forms of a racemic or enantiomerically enriched ester of the formula (I) by a higher rate than the other by an enzyme to give an ester (II) and an acid (III) both with increased enantiomeric purity in a solvent

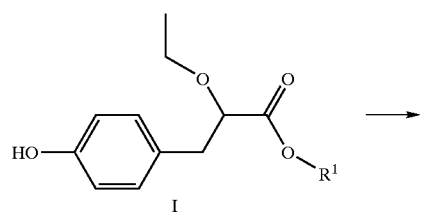

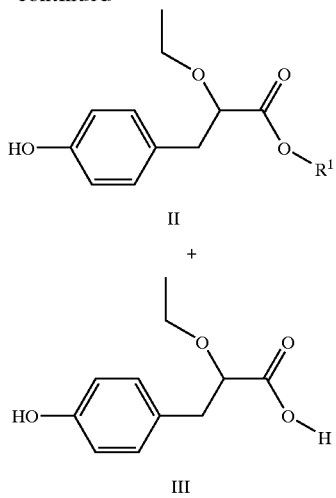

wherein R¹ is defined as straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more selected from halogen(s), —$CF_3$, —CN, —OH, —SH, —COOH, $C_{1-6}$-alkoxy, $C_{1-6}$-alkylthio, —$SCF_3$, —$OCF_3$, —$CONH_2$, —$CSNH_2$, or —NXY, wherein X and Y independently are defined as hydrogen or $C_{1-4}$-alkyl, or R is optionally substituted with phenyl or phenoxy wherein phenyl or phenoxy is optionally substituted with one or more groups selected from halogen(s), —OH, —SH, —COOH, —NXY, —$CF_3$, —CN, $C_{1-4}$-alkyl, $C_{1-4}$-alkoxy, $C_{1-4}$-alkylthio, —SCF, —$OCF_3$, —$CONH_2$ or —$CSNH_2$.

2. The process according to claim 1, wherein R¹ is straight or branched $C_{1-30}$-alkyl, straight or branched $C_{2-30}$-alkenyl, straight or branched $C_{2-30}$-alkynyl, straight or branched $C_{4-30}$-alkenynyl, each of which is optionally substituted with one or more groups selected from halogen(s), —$CF_3$, —OH, —SH, —COOH, $C_{1-6}$-alkoxy, $C_{1-6}$-alkylthio, —$CONH_2$, or —NXY, wherein X and Y independently are defined as hydrogen or $C_{1-6}$-alkyl, or R¹ is optionally substituted with phenyl or phenoxy wherein phenyl or phenoxy is optionally substituted with one or more groups selected from halogen(s), —OH, —SH, —COOH, —NXY, —$CF_3$, $C_{1-4}$-alkyl, $C_{1-4}$-alkoxy, $C_{1-4}$-alkylthio, or —$CONH_2$.

3. The process according to claim 1 wherein R¹ is straight or branched $C_{1-12}$-alkyl, straight or branched $C_{2-12}$-alkenyl, straight or branched $C_{2-12}$-alkynyl, straight or branched $C_{4-10}$-alkenynyl each of which is optionally substituted with one or more groups selected from $CF_3$, —OH, —SH, $C_{1-6}$-alkoxy, or C16-alkylthio.

4. The process according to claim 3 wherein R¹ is straight or branched $C_{1-10}$-alkyl optionally substituted with one or more $C_{1-6}$-alkoxy groups.

5. The process according to claim wherein R¹ is methyl, ethyl, 1-propyl, 2-propyl, 1-hexyl, or ethoxyethyl.

6. The process according to claim 1 wherein R¹ is straight or branched $C_{1-6}$-alkyl, straight or branched $C_{2-8}$-alkenyl, straight or branched $C_{2-8}$-alkynyl, straight or branched $C_{4-10}$-alkenynyl each of which is optionally substituted with one or more groups selected from $CF_3$, —OH, —SH, $C_{1-6}$-alkoxy, or $C_{1-6}$-alkylthio.

7. The process according to claim 1 wherein the enzymatic hydrolysis runs between pH 3–9 at 5–80° C. in buffered or non-buffered water to which is optionally added an organic, water-miscible, co-solvent.

8. The process according to claim 7 wherein the enzymatic hydrolysis runs between pH 5–7 at 20–30° C. in buffered or non-buffered water to which is optionally added an organic, water-miscible, co-solvent selected from the group consisting of acetone, tetrahydrofuran, 2-propanol, ethanol, t-butanol, dimethylformamide, and dimethylsulfoxide.

9. The process according to claim 1 wherein the solvent is an organic solvent, a mixture of organic solvents, water containing salts buffered or not buffered, a two phase system comprising an organic and an aqueous phase, an emulsion or suspension.

10. The process according to claim 1 wherein the enzyme is a protease.

11. The process according to claim 10 wherein the protease is selected from the group consisting of:
(i) a commercial protease selected from the group consisting of Subtilisin carlsberg, Subtilisin 147, pepsin from Rhizo mucor meihei, Subtilisin 309 M1216A, S189E, Subtilisin 309, and Subtilisin PB92 S99G, V102;
(ii) a protease derived from Aspergillus, Rhizopus, *Bacillus alcalophilus, Bacillus cereus, Nocardiopsis natto, Bacillus vulgatus, Bacillus mycoide,* or *Nocardiopsis dassonville;*
(iii) a serine protease comprising a mutant of a *Bacillus subtilisin;* and
(v) a protease selected from the group consisting of:
Protease A or Protease B,
Protease 2 or Aspergillopepsin I from *Aspergillus aculeatus,*
A protease from *Bacillus clausi,*
Trypsin like protease from *Fusarlum oxysporum,*
Alp protease or oryzin from *Aspergillus oryzea,*
Protease 2A from *Aspergillus oryzea,*
C-component from *Bacillus licheniformis,*
Protease 1 or Aspergillopepsin II from *Aspergillus aculeatus,*
NpI protease, Neutral proteinase 1 or Fungalysin from *Aspergillus oryzea,*
NpII protease from *Aspergillus oryzea,*
Pepsin A protease from *Aspergillus oryzea,*
PD 498 protease from Bacillus,
Glycine specific protease from papaya,
alpha-chymotrypsin type II from bovine pancreas,
alpha-chymotrypsin type VII from bovine pancreas,
Proteinase 2A from *Aspergillus oryzae,*
Protease from *Pseudomonas putida,*
Proteinase 6 from *Aspergillus oryzae,* and
A protease from *Aspergillus oryzae,*

12. The process according to claim 10 wherein the protease is produced by or can be isolated from Aspergillus, Bacillus, Fusarium, papaya, or bovine pancreas.

13. The process according to claim 1 wherein the enzyme is a lipase.

14. The process according to claim 13 wherein the lipase is derived from an organism selected from yeast, bacteria, and fungi.

15. The process according to claim 13 wherein the enzyme is a cutinase.

16. The process according to claim 15 wherein the cutinase is from *Fusarium solani* pisi or *Humicola insolens.*

17. The process according to claim 13 wherein the enzyme is a phospholipase.

18. The process according to claim 1 wherein the enzyme is an esterase.

19. The process according to claim 18 wherein the esterase is an esterase from rabbit liver, an esterase from porcine liver, an esterase from hog pancreas, an esterase from hog liver, an esterase type V-S from electric eel, or an esterase from *Pseudomonas putida*.

20. The process according to claim 18 wherein the esterase is produced by Aspergillus.

21. The process according to claim 18 wherein the esterase is produced by *Aspergillus aculeatus* is produced by *Aspergillus nigers* is produced by *Aspergillus oryzae*, is produced by *Aspergillus oryzae*, is produced by *Aspergillus niger* and *Aspergillus aculeatus*, is produced by *Aspergillus niger* or is a pectin methyl esterase from *Aspergillus aculeatus*.

22. The process according to claim 1 wherein the enzyme comprises a mixture of two or more hydrolytic enzymes selected from the group consisting of a protease, a lipase, an esterase, a cutinase, and a phospholipase.

23. The process according to claim 1 wherein $R^1$ is straight or branched $C_{1-6}$-alkyl or ethoxyethyl, the enzyme is a hydrolase from *Aspergillus aculeatus* or *Aspergillus oryzae* or an esterase from *Aspergillus aculeatus* or *Aspergillus oryzae,* the pH of the reaction mixture is from 4 to 8, the reaction mixture contains water and from 0 to 15% organic solvent, and the temperature is from 15 to 40° C.

24. The process according to claim 1 wherein $R^1$ is straight or branched $C_{1-3}$-alkyl or ethoxyethyl, the enzyme is a hydrolase from *Aspergillus aculeatus* or *Aspergillus oryzae* or an esterase from *Aspergillus aculeatus* or *Aspergillus oryzae,* the pH of the reaction mixture is from 5 to 7, the reaction mixture contains water and from 0 to 5% organic solvent, and the temperature is from 20 to 30° C.

25. The process according to claim 1, wherein the solvent is a mixture of (i) an organic solvent and mixtures of organic solvents and (ii) water.

26. The process according to claim 25, wherein said water contains salt and/or buffer.

* * * * *